US011211608B2

(12) United States Patent
Seferos et al.

(10) Patent No.: US 11,211,608 B2
(45) Date of Patent: Dec. 28, 2021

(54) BIO-INSPIRED POLYFLAVIN ELECTRODES FOR ENERGY STORAGE DEVICES

(71) Applicant: THE GOVERNING COUNCIL OF THE UNIVERSITY OF TORONTO, Toronto (CA)

(72) Inventors: Dwight Seferos, Mississauga (CA); Tyler Brian Schon, Toronto (CA); Colin Richard Bridges, Goleta, CA (US)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 322 days.

(21) Appl. No.: 16/072,041

(22) PCT Filed: Feb. 1, 2017

(86) PCT No.: PCT/CA2017/050114
§ 371 (c)(1),
(2) Date: Jul. 23, 2018

(87) PCT Pub. No.: WO2017/132763
PCT Pub. Date: Aug. 10, 2017

(65) Prior Publication Data
US 2019/0036124 A1 Jan. 31, 2019

Related U.S. Application Data

(60) Provisional application No. 62/290,228, filed on Feb. 2, 2016.

(51) Int. Cl.
*H01M 4/60* (2006.01)
*H01M 10/0525* (2010.01)
*H01M 10/054* (2010.01)
*C07D 519/00* (2006.01)
*C08G 61/08* (2006.01)
*C08G 61/12* (2006.01)

(52) U.S. Cl.
CPC .......... *H01M 4/608* (2013.01); *C07D 519/00* (2013.01); *C08G 61/08* (2013.01); *C08G 61/12* (2013.01); *H01M 10/054* (2013.01); *H01M 10/0525* (2013.01); *C08G 2261/149* (2013.01); *C08G 2261/1426* (2013.01); *C08G 2261/3324* (2013.01); *C08G 2261/3342* (2013.01); *C08G 2261/418* (2013.01)

(58) Field of Classification Search
CPC .......... C07D 519/00; C08G 2261/1426; C08G 2261/149; C08G 2261/3324; C08G 2261/3342; C08G 2261/418; C08G 61/08; C08G 61/12; H01M 10/0525; H01M 10/054; H01M 4/608; Y02E 60/10
See application file for complete search history.

(56) References Cited

U.S. PATENT DOCUMENTS

2012/0171563 A1* 7/2012 Kang .................... H01M 10/26
429/199

FOREIGN PATENT DOCUMENTS

EP 2546907 B1 11/2016

OTHER PUBLICATIONS

International Search Report PCT/CA2017/050114, dated May 30, 2017.
Zenkl, E. Stelzer, F., The aqueous ring-opening metathesis polymerization of 7-oxa-norbornene-2, 3 dicarboxylic acid dimethyl ester and norbornene with Ru catalysts, 1992, vol. 76, pp. 1-14.
Welna, D. T., Stone, D. A., Allcock, H. R., Lithium-Ion Conductive polymers as Prospective Membranes for Lithium-Seawater Batteries, 2006, Chem. Mater. vol. 18, p. 4486-4492.
Vygodskii, Y. S., Shaplov, S. A., Lozinskaya, E. I., Lyssenko, K. A., Golovanov, D. G., Malyshkina, InnaA. Gavrilova, N. D., Buchmeiser, M. R., Conductive Polymer Electrolytes Derived from Poly(norbonene)s with Pendant Ionic Imidazolium Moieties, 2008, Macromol. Chem. Phys. vol. 209, pp. 40-51.
Lee, M. , Hong, J., Seo, Dong-Hwa, Nam, D. H. Nam, K. T., Kang, K, and Park, C. B., Redox Cofactor from Biological Energy Transduction as Molecularly Tunable Energy-Storage Compound, 2013, Angew. Chem. Int. Ed. vol. 52, pp. 8322-8328.
Lee, M. Hong, J., Kim, H., Lim, Hee-Dae, Cho, S. B., Kang, K, and Park, C. B., Organic Nanohybrids for Fast and Sustainable Energy Storage, Adv. Mater. 2014, vol. 26, 2558-2565.
Chen, H.; Armand, M.; Demailly, G.; Dolhem, F.; Poizot, P.; Tarascon, J.-M. From Biomass to a Renewable LiXC6O6 Organic Electrode for Sustainable Li-Ion Batteries. ChemSusChem 2008, 1 (4), 348-355.
Lee, M.; Hong, J.; Seo, D.-H.; Nam, D. H.; Nam, K. T.; Kang, K.; Park, C. B. Redox Cofactor From Biological Energy Transduction as Molecularly Tunable Energy-Storage Compound. Angew. Chem., Int. Ed. 2013, 52 (32), 8322-8328.
Nokami, T.; Matsuo, T.; Inatomi, Y.; Hojo, N.; Tsukagoshi, T.; Yoshizawa, H.; Shimizu, A.; Kuramoto, H.; Komae, K.; Tsuyama, H.; Yoshida, J.-I. Polymer-Bound Pyrene-4,5,9,10-Tetraone for Fast-Charge and -Discharge Lithium-Ion Batteries with High Capacity. J. Am. Chem. Soc. 2012, 134 (48), 19694-19700.

(Continued)

*Primary Examiner* — Erich A Leeser
(74) *Attorney, Agent, or Firm* — Hill & Schumacher

(57) ABSTRACT

The present disclosure provides the use of a biomolecule, flavin, appended to a polymerizable unit that can then be polymerized to form an electroactive active polymer. The polymer and the flavin unit are comprised of an organic material containing C, H, N, and O atoms. The electroactive functionality is related to the double bonds that are present in the flavin unit that are appended to a non-electroactive backbone. This appended unit is rendered insoluble in the electrolyte of the discussed secondary battery unit. Several different molecular structures are disclosed exhibiting efficacy as energy storage medium in energy storage devices. Compounds have also been synthesized from which these different energy storage molecular structures are produced.

7 Claims, 14 Drawing Sheets

(56) References Cited

OTHER PUBLICATIONS

Oyaizu, K.; Ando, Y.; Konishi, H.; Nishide, H. Nernstian Adsorbate-Like Bulk Layer of Organic Radical Polymers for High-Density Charge Storage Purposes. J. Am. Chem. Soc. 2008, 130 (44), 14459-14461.

Hong, J.; Lee, M.; Lee, B.; Seo, D.-H.; Park, C. B.; Kang, K. Biologically Inspired Pteridine Redox Centres for Rechargeable Batteries Nat Commun. 2014, 5, 5335.

Jähnert, T.; Häupler, B.; Janoschka, T.; Hager, M. D.; Schubert, U. S. Polymers Based on Stable Phenoxyl Radicals for the Use in Organic Radical Batteries. Macromol. Rapid Commun. 2014, 35 (9), 882-887.

\* cited by examiner

BIO-INSPIRED POLYFLAVIN ELECTRODES FOR ENERGY STORAGE DEVICES

FIELD

The present disclosure relates to an electroactive material that is useful for a secondary battery electrode material and the secondary battery device including the same. Particularly, the present disclosure relates to the use of a biomolecule, flavin, appended to a polymerizable unit that can then be polymerized to form an electroactive active polymer.

BACKGROUND

Sustainable materials for lithium-ion batteries are important due to the widespread use of portable electronics, and the pressing need for grid energy storage and electric vehicles. Traditional lithium-ion batteries use transition metal based cathodes in order to store energy, which not only requires energy intensive processing and extraction methods but also leads to an increased environmental footprint from the toxicity of the waste materials during extraction and synthesis. Additionally, the cost of lithium-ion batteries depends on the cathode material and can account for more than 30% of the cost of the device. An increasingly attractive solution for these problems is the use of organic materials in lithium-ion batteries.

Providing a viable organic material that could be integrated into a lithium-ion battery would be very advantageous.

Patent Literature

PTL 1: European Patent Application No. 12811218.2
PTL 2: European Patent Application No. 11753064.2
PTL 3: U.S. patent application Ser. No. 14/147,671

SUMMARY

As a strategy to decrease the cost of the electrode materials and that associated with multistep synthesis, biomolecules are potentially viable active materials. Taking advantage of the redox activity observed in biological systems, a bio-inspired, semi-synthetic, and cost-effective battery based on these molecules can be constructed. Specifically, flavins are interesting due to their ability to accept two electrons per unit, respectable cell voltage (~2.5V), and high theoretical capacity (~142 mAh g$^{-1}$ for riboflavin). Unfortunately, small molecule or non-polymeric electrodes have a tendency to dissolve in the electrolyte of the assembled secondary battery, rendering them unable to be cycled or hold charge for extended periods.

The present disclosure provides the use of a biomolecule, flavin, appended to a polymerizable unit that can then be polymerized to form an electroactive active polymer. The polymer and the flavin unit comprise of an organic material containing C, H, N, and O atoms. The electroactive functionality is related to the double bonds that are present in the flavin unit that are appended to a non-electroactive backbone. This appended unit is rendered insoluble in the electrolyte of the discussed secondary battery unit.

The present disclosure provides a compound comprising a norbornene having one or more Flavin pendant groups or Flavin derivative groups.

An embodiment of this compound has a molecular structure according to Formula 1;

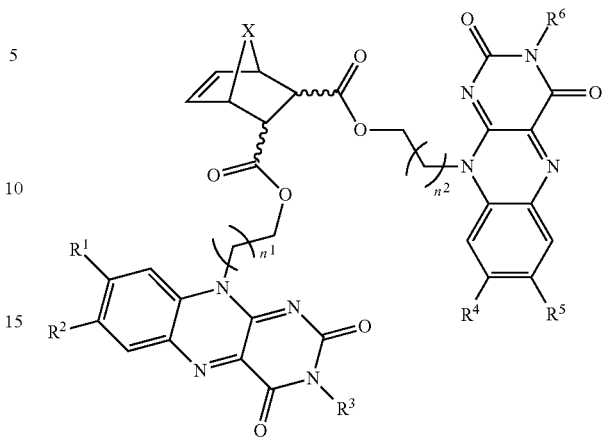

FORMULA 1 wherein $R^1$, $R^2$, $R^4$ and $R^5$ are independently a hydrogen atom, alkyl group, cyano group, nitro group, halogen, aromatic group or heteroaromatic group;

$R^3$ and $R^6$ are independently a hydrogen atom, alkyl group, aromatic group, heteroaromatic group or crosslinking agent;

X is either a carbon or oxygen atom;

$n^1$ and $n^2$ are independently a number of repeat units ranging from 0 to 6.

$R^1$, $R^2$, $R^4$ and $R^5$ may be independently a methyl, ethyl, propyl, isopropyl, or butyl.

$R^3$ and $R^6$ may be independently a methyl, ethyl, propyl, isopropyl, or butyl.

The crosslinking agent is an ester, amide, alkyl, aryl, or any polymer thereof.

In an embodiment $R^1$, $R^2$, $R^3$, $R^4$, $R^5$ and $R^6$ are methyl, X is a methylene, and $n^1$ and $n^2$ is equal to one (1).

In another of a compound comprising a norbornene having one or more Flavin pendant groups or Flavin derivative groups is compound having a molecular structure according to Formula 2;

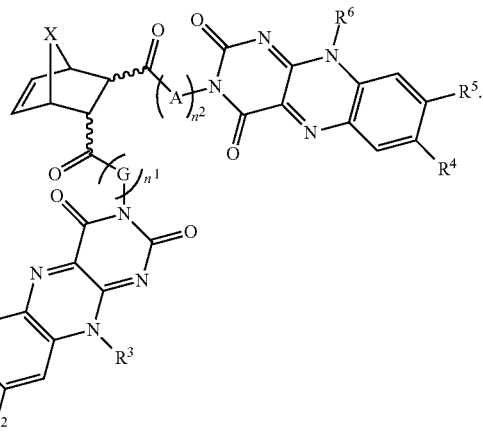

FORMULA 2 wherein $R^1$, $R^2$, $R^4$ and $R^5$ are independently a hydrogen atom, alkyl group, cyano group, nitro group, halogen, aromatic group or heteroaromatic group;

$R^3$ and $R^6$ are independently a hydrogen atom, alkyl group, alcohol group, aromatic group, heteroaromatic group, ester group or crosslinking agent;

X is a carbon or oxygen atom;

A and G are independently a carbon based aliphatic chain having an end functional group that can be used to link the flavin unit through the diimide nitrogen to the norbornene based polymerization unit; and $n^1$ and $n^2$ are independently a number of repeat units of the chain A and G ranging from 0 to 6 in length.

The present disclosure provides an electroactive polymer comprising a poly(norbornene) backbone having Flavin pendant groups or Flavin derivative groups.

A connectivity of the polymer chain is one of a homopolymer, a block copolymer, a gradient copolymer, an alternating copolymer, a semi-random copolymer, or a random copolymer.

An embodiment of these electroactive polymers have a molecular structure according to Formula 3;

FORMULA 3

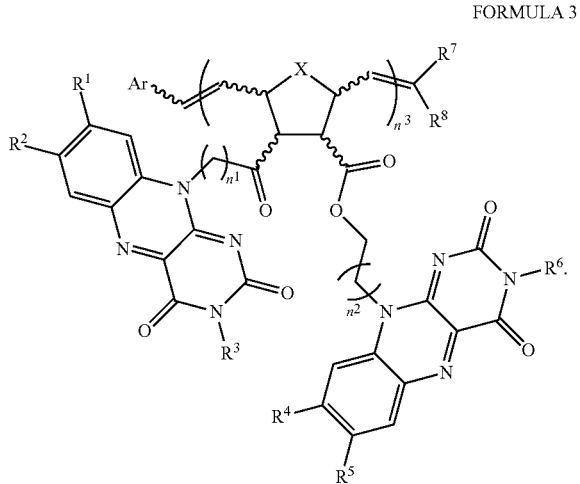

wherein $R^1$, $R^2$, $R^4$, $R^5$, $R^7$, and $R^8$ are independently a hydrogen atom, alkyl group, cyano group, nitro group, halogen, aromatic group or heteroaromatic group;

$R^3$ and $R^6$ are independently a hydrogen atom, alkyl group, aromatic group, heteroaromatic group, ester group or crosslinking agent;

X is either a carbon or oxygen atom;

$n^1$ and $n^2$ are independently a number of repeat units ranging from 0 to 6;

$n^3$ is a number of repeat units ranging from 1 to 1000; and

Ar is an end group that is defined from the ring-opening polymerization catalyst.

The alkyl group of $R^1$, $R^2$, $R^4$, $R^5$, $R^7$, and $R^8$ may be methyl, ethyl, propyl, isopropyl or butyl.

The alkyl group of $R^3$ and $R^6$ may be methyl, ethyl, propyl, isopropyl or butyl.

The crosslinking agent may ester, amide, alkyl, aryl, or any polymer thereof.

The Ar may be phenyl, tolyl, biphenyl or alkenyl.

In an embodiment of the compound $R^1$, $R^2$, $R^3$, $R^4$, $R^5$ and $R^6$ are methyl; $R^7$ and $R^8$ are H, X is a methylene; $n^1$ and $n^2$ are equal to one (1), $n^3$ is ranging between 1 to 1000 and Ar is phenyl.

Another embodiment of these electroactive polymers have a molecular structure of Formula 4;

FORMULA 4

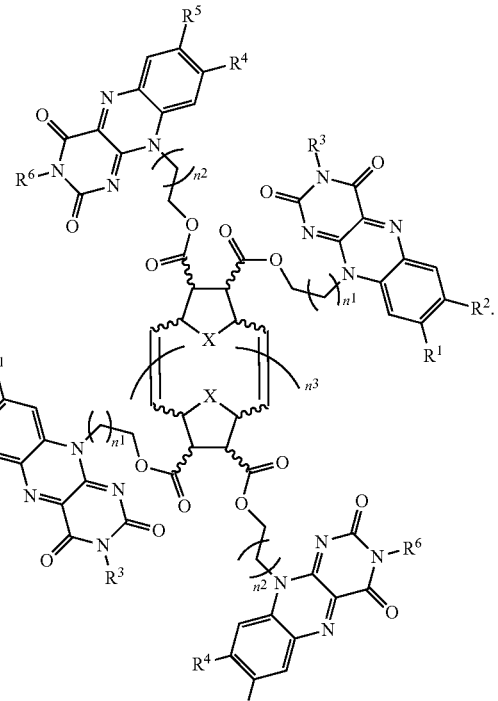

wherein $R^1$, $R^2$, $R^4$, and $R^5$ are independently a hydrogen atom, alkyl group, cyano group, nitro group, halogen, aromatic group or heteroaromatic group;

$R^3$ and $R^6$ are independently a hydrogen atom, alkyl group, aromatic group, heteroaromatic group, ester group or crosslinking agent;

X is either a carbon or oxygen atom;

$n^1$ and $n^2$ are independently a number of repeat units ranging from 0 to 6; and $n^3$ is a number of repeat units ranging from 1 to 1000.

Other embodiments of these electroactive polymer have molecular structures of Formula 5A/B;

FORMULA 5A/B

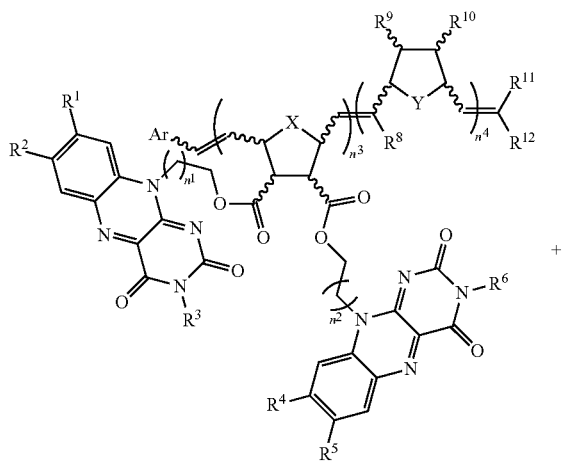

FORMULA 5A

-continued

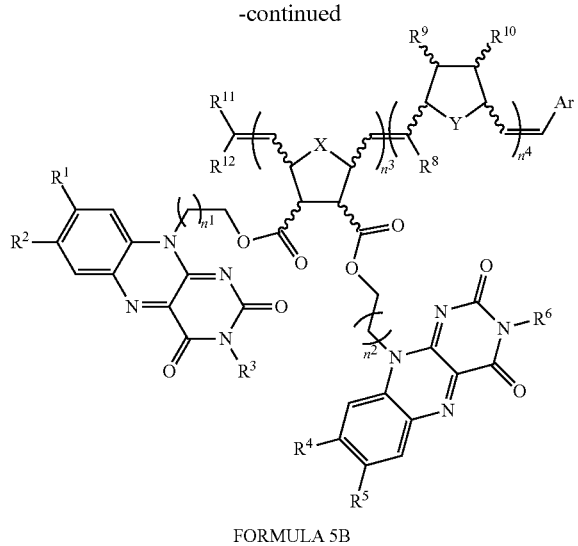

FORMULA 5B wherein $R^1$, $R^2$, $R^4$, $R^5$, $R^8$, $R^{11}$, and $R^{12}$ are independently a hydrogen atom, alkyl group, cyano group, nitro group, halogen, aromatic group or heteroaromatic group;

$R^3$ and $R^6$ are independently a hydrogen atom, alkyl group, aromatic group, heteroaromatic group or crosslinking agent;

$R^9$ and $R^{19}$ are independently a hydrogen atom, alkyl group, a polyether chain to improve ionic conductivity or a conjugated polymer chain to improve electrical conductivity;

X and Y are independently either a carbon or oxygen atom;

$n^1$ and $n^2$ are independently a number of repeat units ranging from 0 to 6;

$n^3$ and $n^4$ are independently a number of repeat units ranging from 1 to 1000; and Ar is an end group defined from the ring-opening polymerization catalyst. Other embodiments of these electroactive polymers have a molecular structure of Formula 6;

FORMULA 6

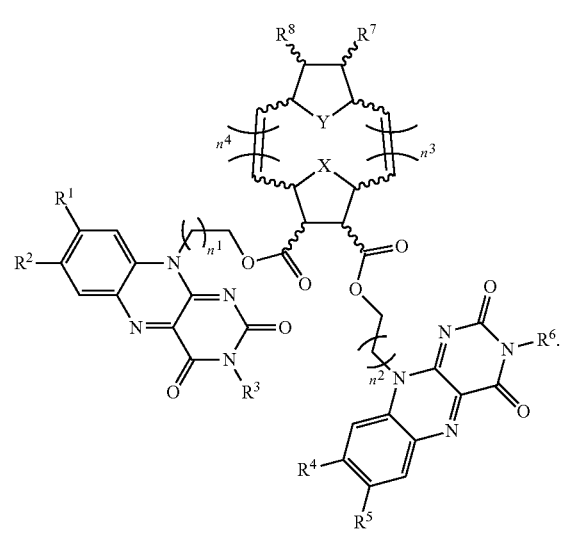

wherein $R^1$, $R^2$, $R^4$, and $R^5$ are independently a hydrogen atom, alkyl group, cyano group, nitro group, halogen, aromatic group or heteroaromatic group;

$R^3$ and $R^6$ are independently a hydrogen atom, alkyl group, aromatic group, heteroaromatic group or crosslinking agent;

$R^7$ and $R^8$ are independently a hydrogen atom, alkyl group, a polyether chain to improve ionic conductivity or a conjugated polymer chain to improve electrical conductivity;

X and Y are independently either a carbon or oxygen atom;

$n^1$ and $n^2$ are independently a number of repeat units ranging from 0 to 6; and $n^3$ and $n^4$ are independently a number of repeat units ranging from 1 to 1000.

Additional embodiments of these electroactive polymers have a molecular structure of Formula 7;

FORMULA 7

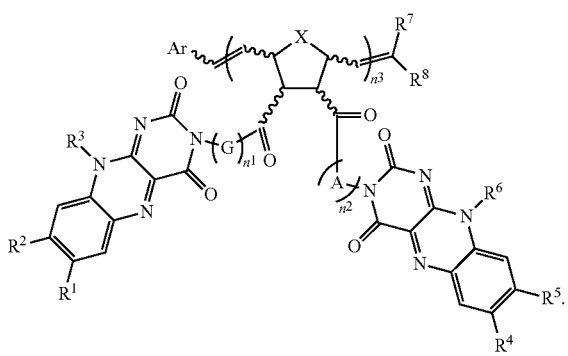

wherein $R^1$, $R^2$, $R^4$, $R^5$, $R^7$, and $R^8$ are independently a hydrogen atom, alkyl group, cyano group, nitro group, halogen, aromatic group or heteroaromatic group;

$R^3$ and $R^6$ are independently a hydrogen atom, alkyl group, alcohol group, aromatic group, heteroaromatic group, ester group or crosslinking agent;

X is either a carbon or oxygen atom;

A and G are independently a carbon based aliphatic chain having an end functional group that can be used to link the flavin unit through the diimide nitrogen to the norbornene based polymerization unit;

$n^1$ and $n^2$ are independently a number of repeat units of the carbon chain A and G ranging from 0 to 6 in length;

$n^3$ is a number of repeat units from 1 to 1000; and

Ar is the end group defined from the ring-opening polymerization catalyst.

Further embodiments of these electroactive polymers have a molecular structure of Formula 8A/B;

FORMULA 8A/B

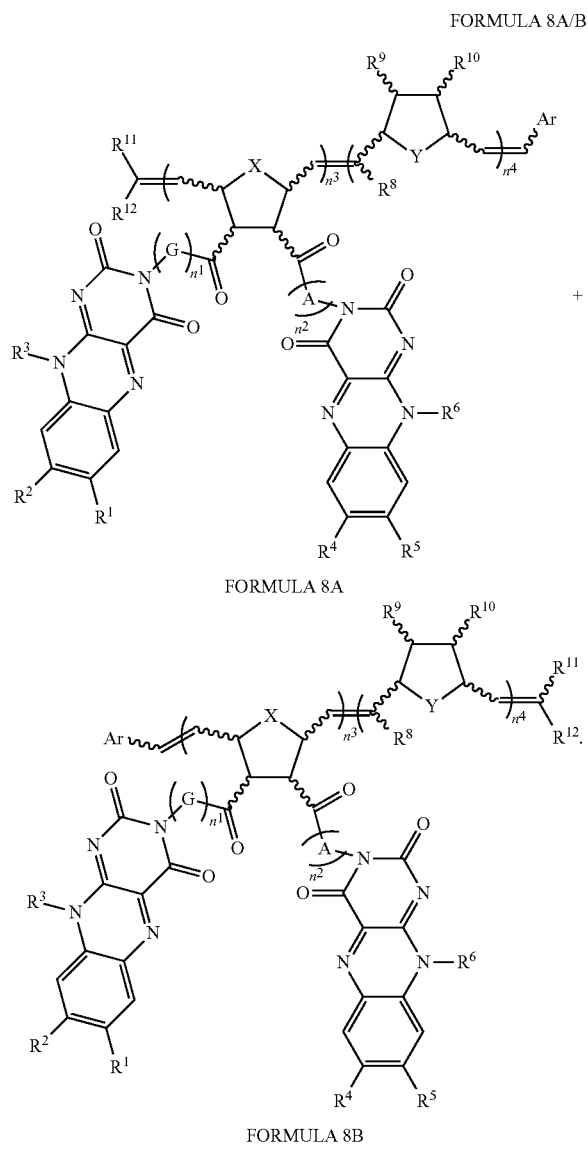

FORMULA 8A

FORMULA 8B wherein $R^1$, $R^2$, $R^4$, $R^5$, $R^8$, $R^{11}$, and $R^{12}$ are independently a hydrogen atom, alkyl group, cyano group, nitro group, halogen, aromatic group or heteroaromatic group;

$R^3$ and $R^6$ are independently a hydrogen atom, alkyl group, alcohol group, aromatic group, heteroaromatic group, ester group or crosslinking agent;

$R^9$ and $R^{15}$ are independently a hydrogen atom, alkyl group, a polyether chain to improve ionic conductivity or a conjugated polymer chain;

X and Y are independently either a carbon or oxygen atom;

A and G are independently a carbon based aliphatic chain having an end functional group that can be used to link the flavin unit through the diimide nitrogen to the norbornene based polymerization unit;

$n^1$ and $n^2$ are independently a number of repeat units of the above mentioned carbon chain A and G ranging from 0 to 6 in length;

$n^3$ and $n^4$ are independently a number of repeat units ranging from 1 to 1000; and Ar is an end group defined from the ring-opening polymerization catalyst.

Additional embodiments of these electroactive polymers have a molecular structure of Formula 9;

FORMULA 9

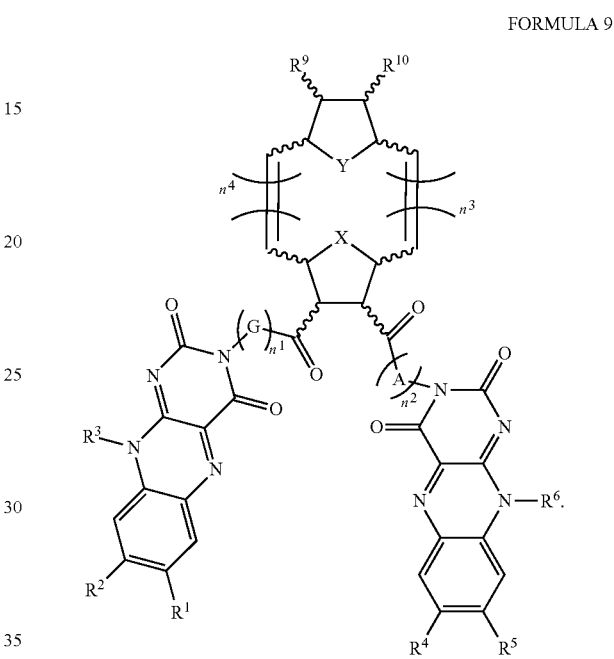

wherein $R^1$, $R^2$, $R^4$, and $R^5$ are independently a hydrogen atom, alkyl group, cyano group, nitro group, halogen, aromatic group or heteroaromatic group;

$R^3$ and $R^6$ are independently a hydrogen atom, alkyl group, aromatic group, heteroaromatic group or crosslinking agent;

$R^9$ and $R^{19}$ are independently a hydrogen atom, alkyl group, a polyether chain to improve ionic conductivity or a conjugated polymer chain to improve electronic conductivity;

X and Y are independently either a carbon or oxygen atom;

A and G are independently a carbon based aliphatic chain having an end functional group that can be used to link the flavin unit through the diimide nitrogen to the norbornene based polymerization unit;

$n^1$ and $n^2$ are independently a number of repeat units of the carbon chain A and G ranging from 0 to 6 in length; and $n^3$ and $n^4$ are independently a number of repeat units ranging from 1 to 1000.

The present disclosure provides a process for producing FORMULA 1, comprising:

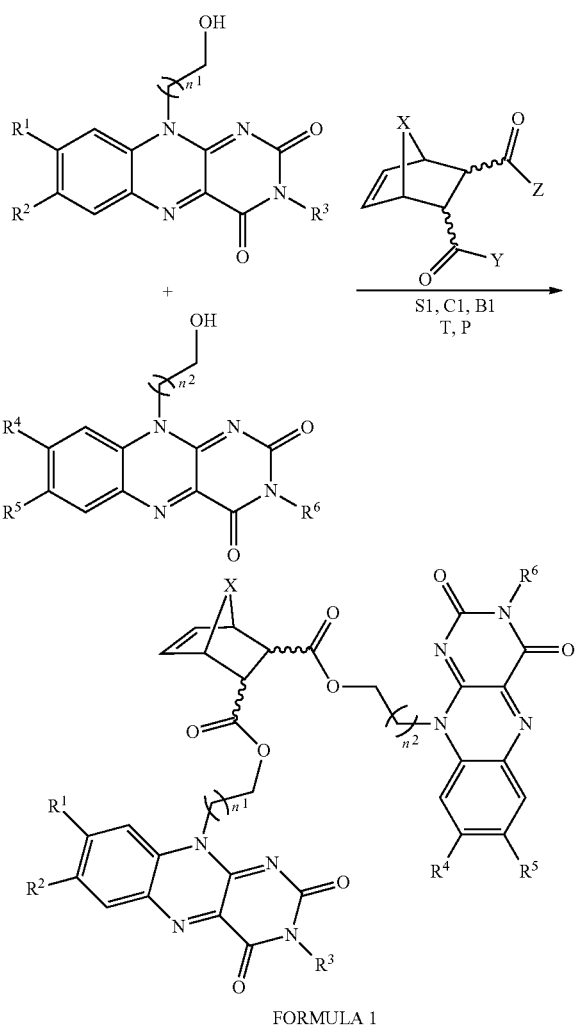

FORMULA 1 wherein $R^1$, $R^2$, $R^4$ and $R^5$ is an hydrogen atom, alkyl group, cyano group, nitro group, halogen, aromatic group or heteroaromatic group;

$R^3$ and $R^6$ is independently a hydrogen atom, alkyl group, aromatic group, heteroaromatic group or crosslinking agent;

X is a carbon or oxygen atom;

$n^1$ and $n^2$ is independently a number of repeat units ranging from 0 to 6;

Z and Y is leaving groups that are eliminated in the reaction and replaced with the flavin groups;

S1 is a solvent;

C1 is a catalyst;

B1 is a base; and the temperature, T, is between −20 and 50 degrees Celsius and the pressure, P, is between 0.5 and 5 atmospheres.

Z and Y may be any one of bromine, chlorine, iodine, tosyl, and/or carboxyl groups.

S1 may be any one or combination of $CHCl_3$, dichloromethane, ether, ethyl acetate, dimethyl formamide, and acetonitrile.

In an embodiment C1 is DMAP.

The base B1 may be any one of pyridine, triethylamine, aniline, indole, piperidine, pyrimidine, pyrrolidine, pyrrole, imidazole, 4-diazabicyclo[2.2.2]octane, and 1,8-diazobicyclo[5.4.0]undec-7-ene.

In embodiments the alkyl group of $R^1$, $R^2$, $R^4$, and $R^5$ is independently a methyl, ethyl, propyl, isopropyl, or butyl.

In embodiments the alkyl group of $R^3$ and $R^6$ is independently a methyl, ethyl, propyl, isopropyl, or butyl.

In an embodiment $R^1$, $R^2$, $R^3$, $R^4$, $R^5$, and $R^6$ may be methyl, X may methylene, $n^1$ and $n^2$ may be equal to one (1), S1 may be $CH_2Cl_2$, C1 may be DMAP, and B1 may be pyridine.

The present disclosure provides a process for producing FORMULA 3 from FORMULA 1, comprising:

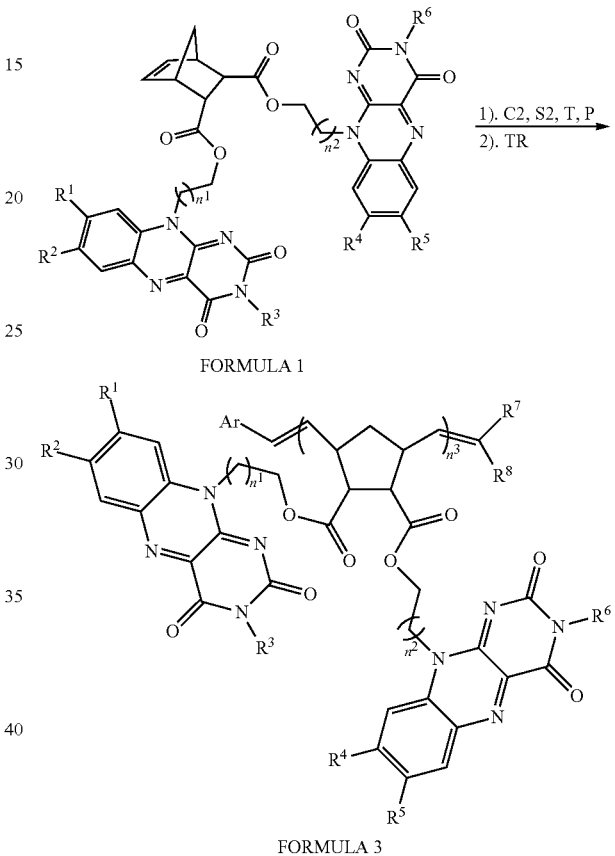

FORMULA 1

FORMULA 3

$R^1$, $R^2$, $R^4$, $R^5$, $R^7$, and $R^8$ are independently a hydrogen atom, alkyl group cyano group, nitro group, halogen, aromatic group or heteroaromatic group;

$R^3$ and $R^6$ is independently a hydrogen atom, alkyl group, aromatic group, heteroaromatic group, ester group or crosslinking agent;

X is either a carbon or oxygen atom;

$n^1$ and $n^2$ is independently a number of repeat units ranging from 0 to 6;

$n^3$ is ranging from 1 to 1000;

Ar is an end group defined from the ring-opening polymerization catalyst;

C2 is a ring-opening metathesis catalyst;

S2 is a solvent;

TR is a terminating reagent; and the temperature, T, is between −20 and 50 degrees Celsius and the pressure, P, is between 0.5 and 5 atmospheres.

$R^1$, $R^2$, $R^4$, $R^5$, $R^7$, and $R^8$ may be independently methyl, ethyl, propyl, isopropyl, or butyl.

$R^3$ and $R^6$ may be independently methyl, ethyl, propyl, isopropyl, or butyl.

Ar may be any one of phenyl, tolyl, biphenyl or alkenyl as defined by the ring-opening metathesis catalyst C2.

C2 may be any one of Grubbs 1, Grubbs 2, Grubbs 3 or molybdenum or tungsten alkylidene type Schrock.

S2 may be anyone of $CHCl_3$, dichloromethane, ether, ethyl acetate, dimethyl formamide, acetonitrile and any combination of the above.

TR is any reactive alkene that will remove the catalyst from the chain, terminating the polymerization and installing the end groups.

In some embodiments TR is anyone of ethyl vinyl ether, propyl vinyl ether, butyl vinyl ether and benzyl vinyl ether.

In an embodiment $R^1$, $R^2$, $R^3$, $R^4$, $R^5$, and $R^6$ are methyl, $R^7$ and $R^8$ are hydrogen, Ar is phenyl, X is methylene, $n^1$ and $n^2$ equal one (1), $n^3$ is in a range between 1 and 1000, C2 is Grubb 2, S2 is $CHCl_3$, TR is ethyl vinyl ether.

The present disclosure provides an energy storage device comprising an electrode material having a molecular structure according to any one or combination of Formula 3, Formula 4, Formula 5, Formula 6, Formula 7, Formula 8, and Formula 9.

The energy storage device may be any one of a lithium-ion battery, a sodium-ion battery, a magnesium-ion battery, an aluminum-ion battery, a potassium-ion battery, a metal-sulfur battery, a metal-air battery, a solid-state battery, a flow battery, an aqueous battery, a capacitor, a supercapacitor, a hybrid device combining electrode materials of any of the above devices, and a thin film battery that includes and of the above mentioned devices with a total device thickness of 5 millimeters but preferably less than 1 millimeter.

In some embodiments the energy storage device may be a battery including an electrolyte, and the electrolyte comprises a salt dissolved in an organic electrolyte.

In some embodiments the energy storage device may be a battery including an electrolyte, and the electrolyte comprises a salt dissolved in an aqueous electrolyte.

In some embodiments the energy storage device may be a battery including an electrolyte, and the electrolyte comprises a salt dissolved in a gel polymer electrolyte with an aqueous or organic solvent.

The energy storage devices may be constructed with flexible mechanical properties and a/or flexible form factor.

A further understanding of the functional and advantageous aspects of the present disclosure can be realized by reference to the following detailed description and drawings.

DETAILED DESCRIPTION

Figure 1:
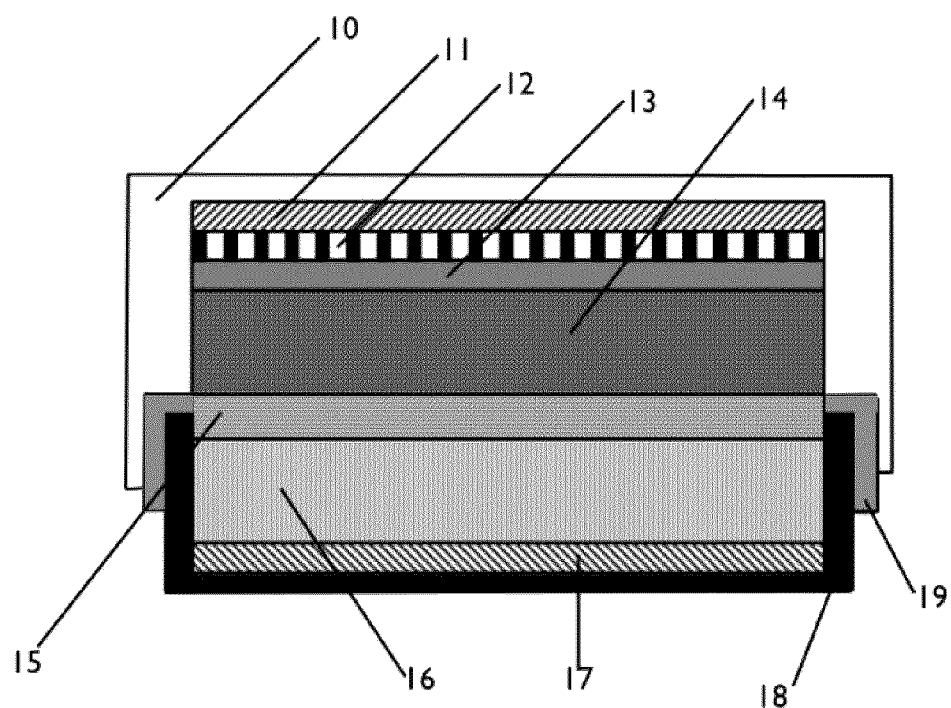
FIG. 1. Scheme representing the battery architecture and incorporation of the electroactive redox polymer into the device. 10 is a cell cathode casing, 11 is a spring spacer that compresses device, 12 is a spacer/current collector, 13 is a substrate that the cathode is cast on, 14 is the cathode, 15 is the separator and electrolyte, 16 is the anode, 17 is the anode spacer/current collector, 18 is a cell anode casing, and 19 is a gasket/O-ring to hermetically seal the device.

Without limitation, the majority of the systems described herein are directed to chemical compounds, their method of synthesis, and polymeric electrode materials produced from the above mentioned compounds for use in energy storage devices. A surprising property of these materials is that they exhibit significant efficacy as energy storage media in energy storage devices. As required, embodiments of the present disclosure are disclosed herein. However, the disclosed embodiments are merely exemplary, and it should be understood that the embodiments of the present disclosure may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present disclosure. For purposes of teaching and not limitation, the illustrated embodiments are directed compounds, their method of synthesis, and electrode materials produced from these compounds for use in energy storage devices.

As used herein, the term "about", when used in conjunction with ranges of dimensions, velocities, temperatures or other physical properties or characteristics is meant to cover slight variations that may exist in the upper and lower limits of the ranges of dimensions as to not exclude embodiments where on average most of the dimensions are satisfied but where statistically dimensions may exist outside this region.

As used herein, the phrase "connectivity" is meant to describe the sequence of the repeating structure of the polymer, whether it is a homopolymer, block copolymer, gradient copolymer, alternating copolymer, semi-random copolymer, or random copolymer.

As used herein, the letter S1 and S2 refers to a solvent.

As used herein, the letter C1 and C2 refers to a catalyst.

As used herein, the letters TR refers to a terminating reagent.

As used herein, the letter B1 refers to a base.

As used herein, the letter T refers to a temperature.

As used herein, the letter P refers to a pressure.

Broadly speaking, the present disclosure provides a compound comprising a norbornene having one or more Flavin pendant groups or Flavin derivative groups. The compound is made by covalently connecting a single norbornene unit to one or more Flavin or Flavin derivatives. This can be accomplished using a variety of synthetic routes. Briefly, the norbornene unit can contain electrophilic center(s) or atom(s) which undergo a nucleophilic substitution or condensation by a nucleophilic functionality present on the Flavin or Flavin derivative. Alternatively, coupling reagents can facilitate bonding between the norbornene and Flavin or Flavin derivative. Appropriate choice of functionality on the norbornene and/or Flavin or Flavin derivative can control the degree of covalent attachment and also the chemical functionality that provides the above mentioned covalent attachment. The advantages of this compound are its ease of synthesis, its high solubility, derivation from sustainable chemicals, its highly electroactive Flavin groups, and its ease of transformation into an insoluble polymeric electroactive material.

The materials disclosed herein have been designed keeping in mind the problems with the existing art as described above. The present disclosure describes the use of a polymeric compound with appended redox active flavin units as an electroactive material for secondary batteries. Due to the ability of flavins to reversibly accept charges at a defined voltage, they are well-suited for energy storage applications. To the best of our knowledge, this is the first report of a pendant polymer using a bio-derived redox unit for battery applications. We show that this polymer provides a capacity of 125 mAh $g^{-1}$ with a voltage of 2.5 V in a device using lithium metal as the anode material.

The present disclosure relates to an electroactive material in an energy storage device that can be derived from the compound having the molecular structure described in Formula 1 given here below:

[FORMULA 1]

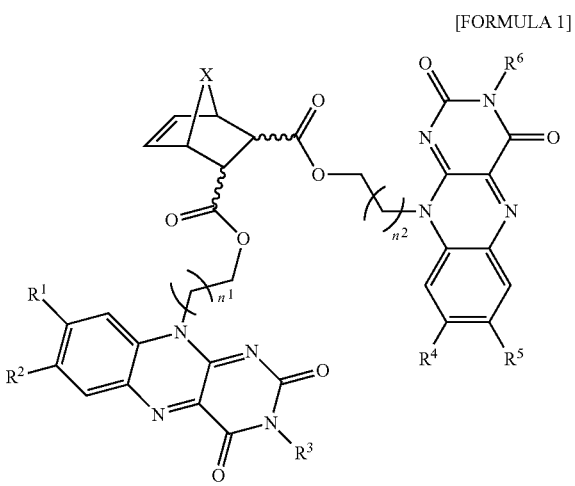

In Formula 1, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6.

Formula 1 can be synthesized through a condensation reaction between a carbonyl group and a functionalized flavin with a free alcohol group as shown below:

[METHOD 1]

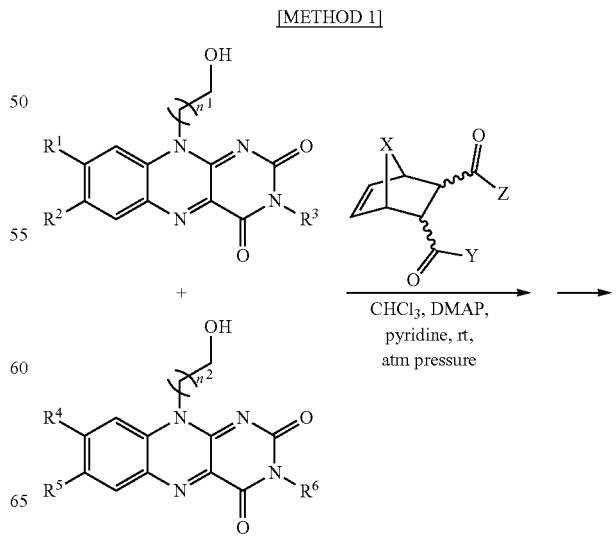

15
-continued

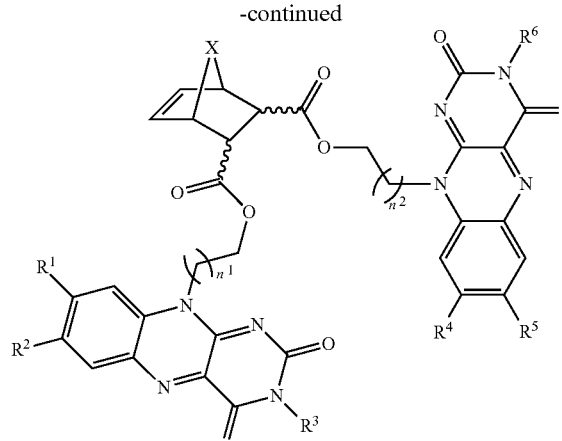

FORMULA 1

In Method 1, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6. Z and Y represent leaving groups that are eliminated in the reaction and replaced with the flavin groups which can be but are not limited to bromine, chlorine, iodine, tosyl, and/or carboxyl groups. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Dimethylamino pyridine (DMAP) acts as a catalyst in order to speed up the reaction rate by reversibly reacting with the norbornene-type electrophile. Pyridine acts as a base in order to remove any acidic protons from the reaction in order to allow it to proceed. The base can also be a number of organic bases including but not limited to triethylamine, aniline, indole, piperidine, pyrimidine, pyrrolidine, pyrrole, imidazole, 4-diazabicyclo[2.2.2]octane, and 1,8-diazobicyclo[5.4.0]undec-7-ene. The temperature can be anywhere between −20 and 50 degrees Celsius and the pressure can be anywhere between 0.5 and 5 atmospheres.

Alternatively, Formula 1 can be made by an acid catalyzed condensation by Method 2:

16

[METHOD 2]

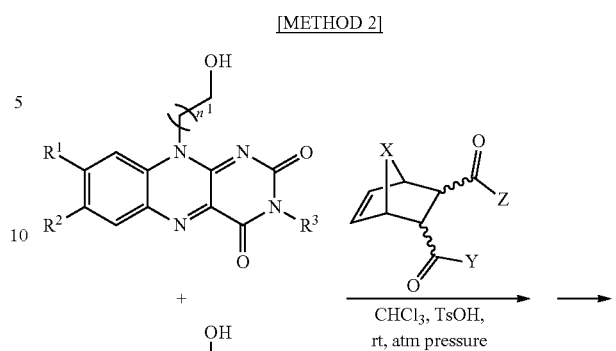

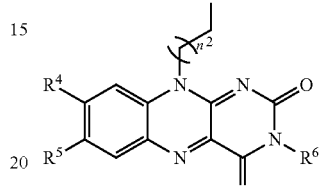

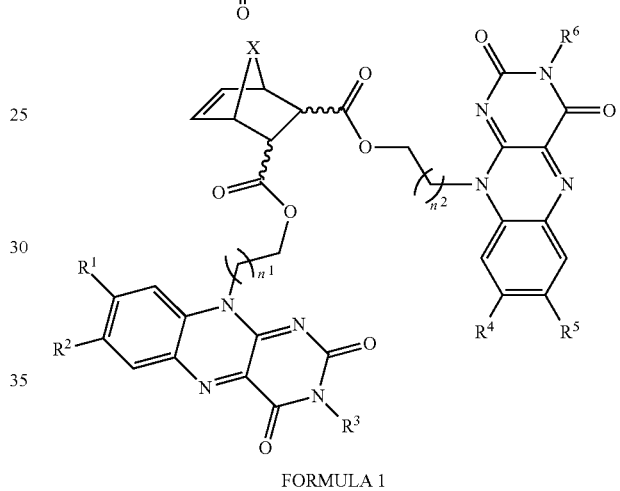

FORMULA 1

In Method 2, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6. Y and Z represent leaving groups that will be eliminated from the reaction and replaced with the flavin group which can be but are not limited to a hydroxyl group, an alkoxide group such as methoxide, ethoxide, isopropoxide and/or propoxide. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Para-toluenesulfonic acid (TsOH) is an acid catalyst that protonates the carbonyl group to allow it to become a better electrophile. The acid catalyst can be but is not limited to triflic acid, sulfuric acid, hydrochloric acid, or hydrobromic acid. The temperature can be anywhere between −20 and 100 degrees Celsius and the pressure can be anywhere between 0.5 and 5 atmospheres.

Formula 1 can also by synthesized through a coupling reaction between a free alcohol on the flavin unit and the free carboxylic acid on the norbornene derivative as described in Method 3:

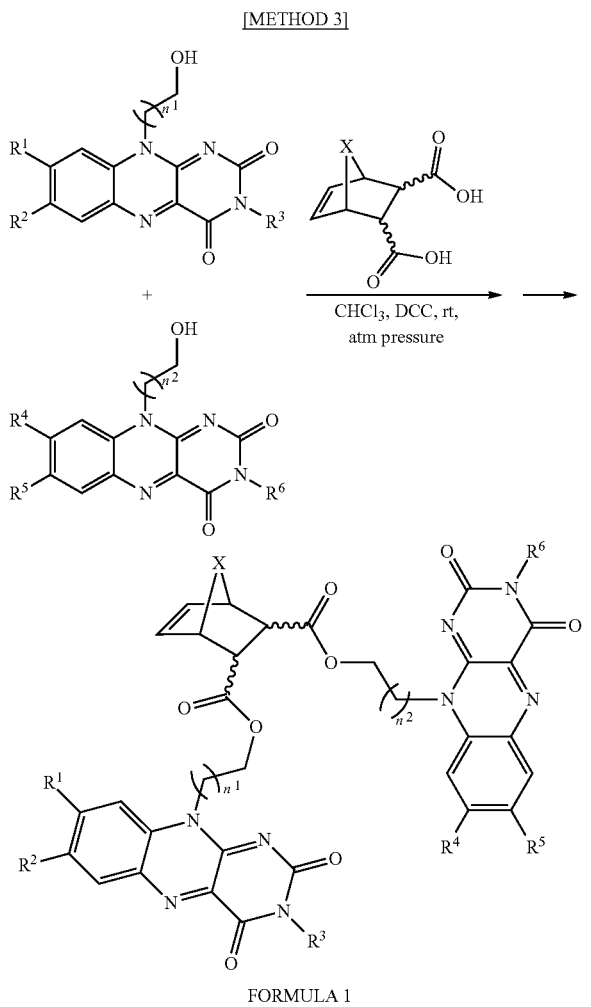

FORMULA 1

In Method 3, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. N,N'-dicyclohexylcarbodiimide (DCC) is a coupling reagent that couples the free alcohol and the carboxylic acid in order form an ester. This coupling reagent can be but is not limited to N—N'-diisopropylcarbodiimide, ethyl-(N',N'-dimethylamino)propylcarbodiimide hydrochloride, benzotriazol-1-yloxy)tris(dimethylamino)phosphonium hexafluorophosphate, or 0-(benzotriazol-1-yl)-N,N,N',N'-tetramethyluronium hexafluorophosphate. The temperature can be anywhere between −20 and 50 degrees Celsius and the pressure can be anywhere between 0.5 and 5 atmospheres.

Formula 1 can also be synthesized by a reaction between the norbornene derivative anhydride and the free alcohol on the flavin unit described in Method 4:

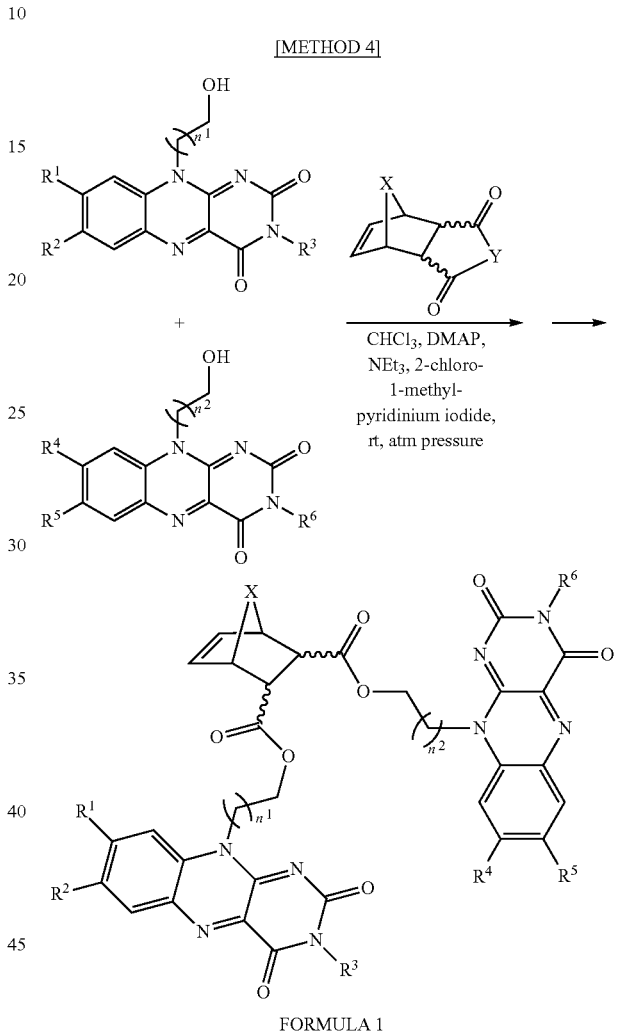

FORMULA 1

In Method 4, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6. Y denotes either an oxygen atom or a sulfur atom. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Dimethylamino pyridine (DMAP) acts as a catalyst in order to speed up the reaction rate by reversibly reacting with the norbornene-type electrophile. Triethyl amine (NEt$_3$) acts as a base in order to remove any acidic protons from the reaction in order to allow it to proceed. The base can also be a number of organic bases including but not limited to pyridine, aniline, indole, piperidine, pyrimidine, pyrrolidine, pyrrole, imidazole, 4-diazabicyclo[2.2.2]octane, and 1,8-diazobicyclo[5.4.0]undec-7-ene. 2-chloro-1-methylpyridinium iodide is a coupling reagent that links together the carboxylate intermediate and the free alcohol on the flavin. The temperature can be anywhere between −20 and 50 degrees Celsius and the pressure can be anywhere between 0.5 and 5 atmospheres.

Alternatively, the electroactive material can be derived from a compound that has the molecular structure described in Formula 2:

[FORMULA 2]

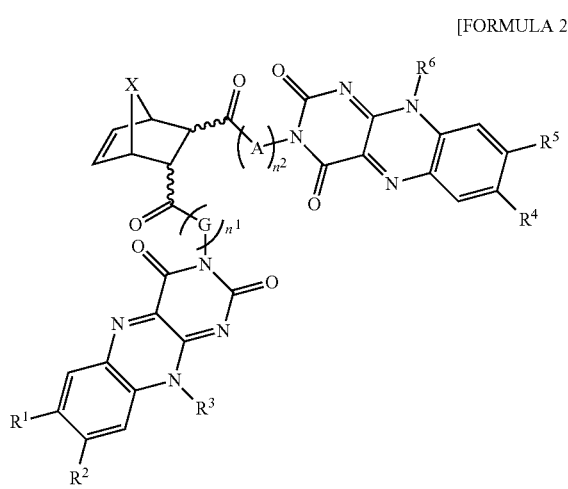

In Formula 2, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). X denotes either a carbon or oxygen atom. A and G each denote independently a carbon based aliphatic chain that has an end functional group such as, but not limited to, hydroxyl and amino that can be used to link the flavin unit through the diimide nitrogen to the norbornene based polymerization unit. Here $n^1$ and $n^2$ each denote independently a number of repeat units of the above mentioned chain A and G ranging from 0 to 6 in length.

Formula 2 can be synthesized by reacting the a functionalized flavin with a free diimide nitrogen with a carbonyl group on the norbornene unit as describe in Method 5:

[METHOD 5]

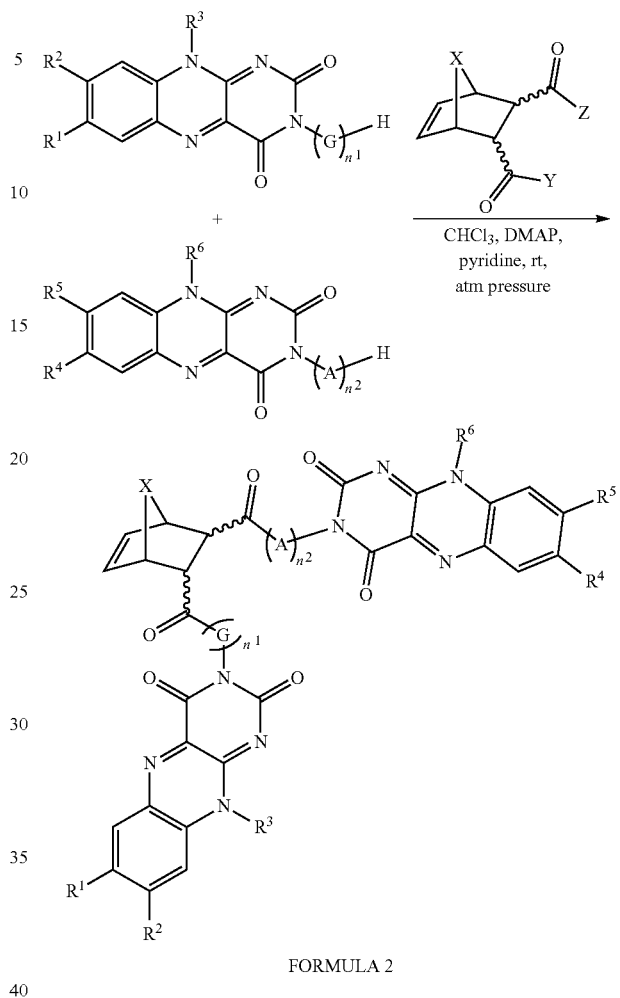

FORMULA 2

In Method 5, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). X denotes either a carbon or oxygen atom. A and G each denote independently a carbon based aliphatic chain that has an end functional group such as, but not limited to, hydroxyl and amino that can be used to link the flavin unit through the diimide nitrogen to the norbornene based polymerization unit. Here $n^1$ and $n^2$ each denote independently a number of repeat units of the above mentioned chain A and G ranging from 0 to 6 in length. Z and Y represent leaving groups that are eliminated in the reaction and replaced with the flavin groups which can be but are not limited to bromine, chlorine, iodine, tosyl, carboxyl groups. CHCl$_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Dimethylamino pyridine (DMAP) acts as a catalyst in order to speed up the reaction rate by reversibly reacting with the norbornene-type electrophile. Pyridine acts as a base in order to remove any acidic protons from the reaction in order to allow it to proceed. The base can also be a number of organic bases including but not limited to triethylamine, aniline, indole, piperidine, pyrimidine, pyrrolidine, pyrrole, imidazole, 4-diazabicyclo[2.2.2]octane, and 1,8-diazobicyclo[5.4.0]undec-7-ene. The temperature can be anywhere between −20 and 50 degrees Celsius and the pressure can be anywhere between 0.5 and 5 atmospheres.

Additionally, Formula 2 can be synthesized by an acid catalyzed condensation as described in Method 6:

[METHOD 6]

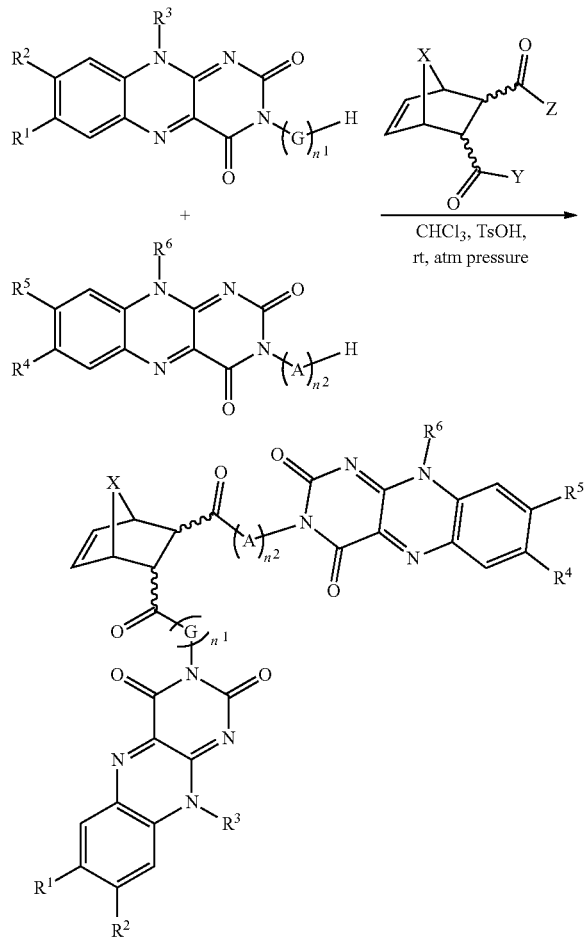

FORMULA 2

In Method 6, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). X denotes either a carbon or oxygen atom. A and G each denote independently a carbon based aliphatic chain that has an end functional group such as, but not limited to, hydroxyl and amino that can be used to link the flavin unit through the diimide nitrogen to the norbornene based polymerization unit. Here $n^1$ and $n^2$ each denote independently a number of repeat units of the above mentioned chain A and G ranging from 0 to 6 in length. Y and Z represent leaving groups that will be eliminated from the reaction and replaced with the flavin group which can be but are not limited to a hydroxyl group, an alkoxide group such as methoxide, ethoxide, isopropoxide or propoxide. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Para-toluenesulfonic acid (TsOH) is an acid catalyst that protonates the carbonyl group to allow it to become a better electrophile. The acid catalyst can be but is not limited to triflic acid, sulfuric acid, hydrochloric acid, or hydrobromic acid. The temperature can be anywhere between −20 and 100 degrees Celsius and the pressure can be anywhere between 0.5 and 5 atmospheres.

Formula 2 can also by synthesized through a coupling reaction between a free alcohol on the flavin unit and the free carboxylic acid on the norbornene derivative as described in Method 7:

[METHOD 7]

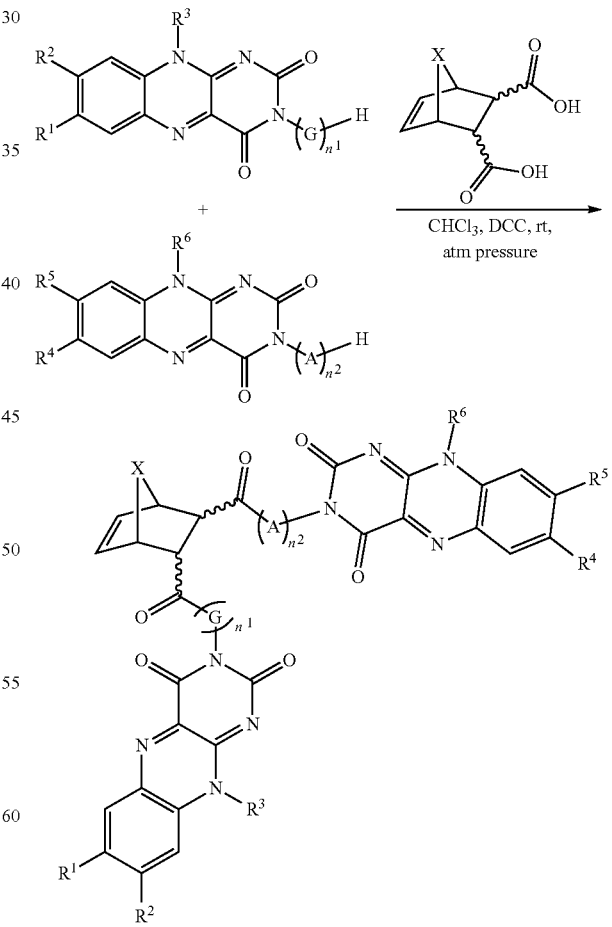

FORMULA 2

In Method 7, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). X denotes either a carbon or oxygen atom. A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. N,N'-dicyclohexylcarbodiimide (DCC) is a coupling reagent that couples the free functional group on the end of A and G to the carboxylic acid. This coupling reagent can also be but is not limited to N—N'-diisopropylcarbodiimide, ethyl-(N',N'-dimethylamino)propylcarbodiimide hydrochloride, benzotriazol-1-yloxy)tris(dimethylamino)phosphonium hexafluorophosphate, or O-(benzotriazol-1-yl)-N,N,N',N'-tetramethyluronium hexafluorophosphate. The temperature can be anywhere between −20 and 50 degrees Celsius and the pressure can be anywhere between 0.5 and 5 atmospheres.

Formula 2 can also be synthesized by a reaction between the norbornene derivative anhydride and the free alcohol on the flavin unit described in Method 8:

[METHOD 8]

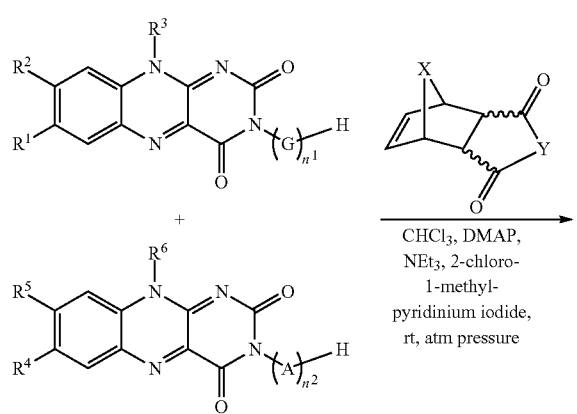

CHCl₃, DMAP, NEt₃, 2-chloro-1-methyl-pyridinium iodide, rt, atm pressure

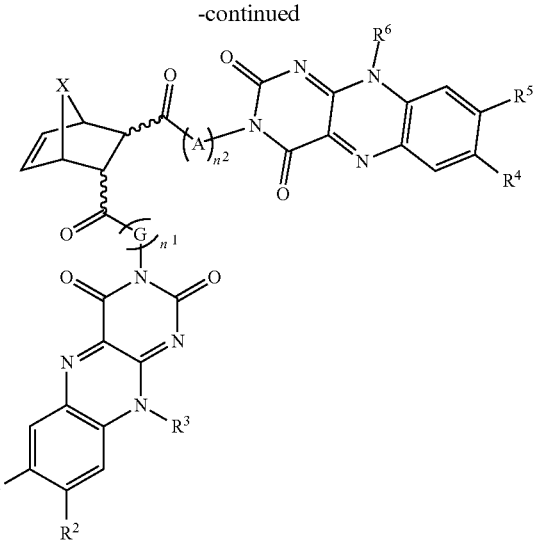

FORMULA 2

In Method 8, $R^1$, $R^2$, $R^4$ and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). X denotes either a carbon or oxygen atom. A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. Y denotes either an oxygen or sulfur atom. $CHCl_3$ acts as the solvent and allows the reagents to react together without reacting itself with any of the reagents.

The solvent could also be, but is not limited to, dichloromethane, ether, ethyl acetate, dimethyl formamide, acetonitrile and any combination of the above. Dimethylamino pyridine (DMAP) acts as a catalyst in order to speed up the reaction rate by reversibly reacting with the norbornene-type electrophile. Triethyl amine ($NEt_3$) acts as a base in order to remove any acidic protons from the reaction in order to allow it to proceed. The base can also be a number of organic bases including but not limited to pyridine, aniline, indole, piperidine, pyrimidine, pyrrolidine, pyrrole, imidazole, 4-diazabicyclo[2.2.2]octane, and 1,8-diazobicyclo[5.4.0]undec-7-ene. 2-chloro-1-methylpyridinium iodide is a coupling reagent that links together the carboxylate intermediate and the free alcohol on the flavin. The temperature can be anywhere between −20 and 50 degrees Celsius and the pressure can be anywhere between 0.5 and 5 atmospheres.

The electroactive material described in the present disclosure can have the structure according to Formula 3 if the material is derived from Formula 1:

[FORMULA 3]

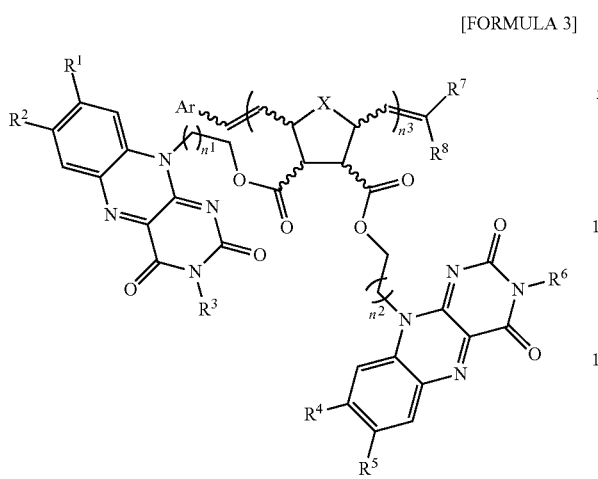

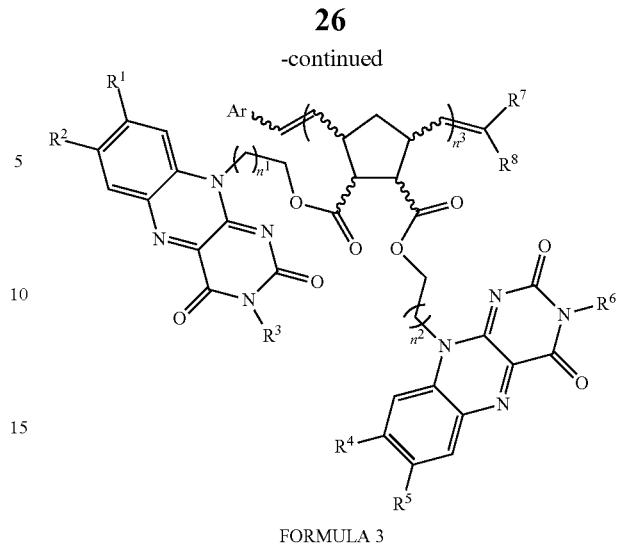

FORMULA 3

In Formula 3, $R^1$, $R^2$, $R^4$, $R^5$, $R^7$, and $R^8$ each denote independently a hydrogen atom, alkyl group (including but not limited to methyl, ethyl, propyl, isopropyl, butyl), cyano group, nitro group, halogen, aromatic group or heteroaromatic group $R^3$ and $R^6$ each denote independently a hydrogen atom, alkyl group (including but not limited to methyl, ethyl, propyl, isopropyl, butyl), aromatic group, heteroaromatic group, ester group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6. The repeat structure described by $n^3$ is any number of units ranging from 1 to 1000. Ar denotes the end group that is defined from the ring-opening polymerization catalyst that includes, but is not limited to, phenyl, tolyl, biphenyl or alkenyl. The connectivity of the polymer chain is one of a homopolymer, a block copolymer, a gradient copolymer, an alternating copolymer, a semi-random copolymer, or a random copolymer.

Formula 3 can be synthesized by subjecting Formula 1 to ring-opening metathesis polymerization conditions as described in Method 9:

[METHOD 9]

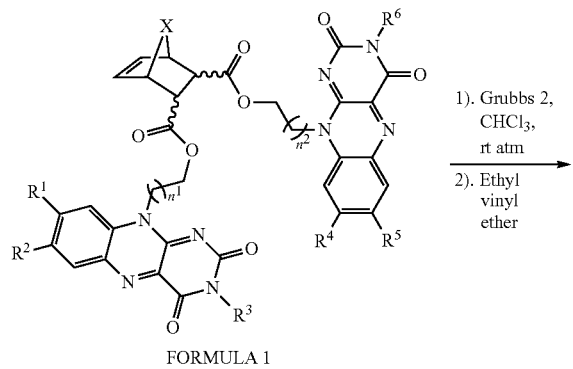

1). Grubbs 2, CHCl$_3$, rt atm
2). Ethyl vinyl ether

FORMULA 1

In Method 9, $R^1$, $R^2$, $R^4$, $R^5$, $R^7$, and $R^8$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group, ester group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6. The repeat structure described by $n^3$ is any number of units ranging from 1 to 1000. Ar denotes the end group that is defined from the ring-opening polymerization catalyst that includes, but is not limited to, phenyl, tolyl, biphenyl or alkenyl.

The connectivity of the polymer chain is one of a homopolymer, a block copolymer, a gradient copolymer, an alternating copolymer, a semi-random copolymer, or a random copolymer. The Grubbs 2 catalyst is a ring-opening metathesis catalyst, also referred to as an olefin metathesis catalyst, that is used to ring-open the norbornene based cyclic alkene and sequentially add monomer units to the growing chain in an olefin metathesis fashion in a controlled or uncontrolled manner. Here, controlled or uncontrolled refer to the ability to control, or not, the molecular weight or dispersity of the molecular weights of the resultant polymer. This Grubbs 2 catalyst can be substituted for any ring-opening metathesis catalyst that can include, but is not limited to, ruthenium carbene type catalysts such as Grubbs 1, Grubbs 3 or molybdenum or tungsten alkylidene type Schrock catalysts provided that they do not interfere or destroy the functionality on the monomer chains. CHCl$_3$ acts as the solvent and allows the reagents to react together without reacting itself with any of the reagents.

The solvent could also be, but is not limited to, dichloromethane, ether, ethyl acetate, dimethyl formamide, acetonitrile and any combination of the above. Ethyl vinyl ether is the terminating or end-capping reagent that acts to remove the catalyst from the growing polymer chain and replace it with an alkene with the appropriate substitutions $R^7$ and $R^8$. This terminating agent can be replaced with any reactive alkene that will remove the catalyst from the chain, terminating the polymerization and install the above mentioned end groups such as, but not limited to, propyl vinyl ether, butyl vinyl ether and benzyl vinyl ether. The temperature can be anywhere between −20 and 50 degrees Celsius and the pressure can be anywhere between 0.5 and 5 atmospheres. In an embodiment, the compound of Formula 3 has $R^1$, $R^2$, $R^3$, $R^4$, $R^5$, and $R^6$ are methyl, $R^7$ and $R^8$ are hydrogen, Ar is phenyl, X is methylene, n' and $n^2$ equal one (1), $n^3$ is in a range between 1 and 1000.

The compound was readily synthesized from either commercially available chemicals or easily synthesized compounds under mild reaction conditions that do not require air or moisture-free conditions. The compound also has superior performance as an electrode material in an energy storage due to its high capacity owing to its minimal electrochemically inactive mass, superior voltage, ease of processing, and insolubility in the battery electrolyte. This embodiment is identified as the best performing electroactive material under our testing conditions.

Method 9 can also produce cyclic polymers as a result of back-biting of the catalyst giving compounds with the structure described in Formula 4:

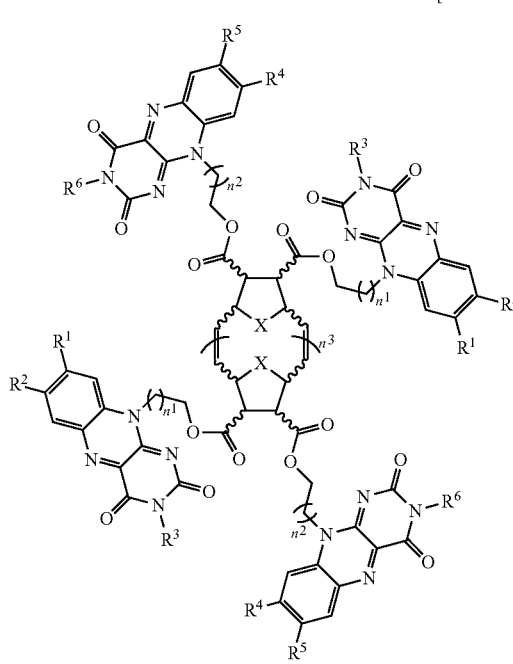

[FORMULA 4]

In Formula 4, $R^1$, $R^2$, $R^4$, and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group, ester group or crosslinking agent (including but not limited to ester, amide, alkyl, aryl, or any polymer thereof). X denotes either a carbon or oxygen atom. Here $n^1$ and $n^2$ each denote independently a number of repeat units ranging from 0 to 6. The repeat structure described by $n^3$ is any number of units ranging from 1 to 1000. The connectivity of the polymer chain is one of a homopolymer, a block copolymer, a gradient copolymer, an alternating copolymer, a semi-random copolymer, or a random copolymer.

In the case where in Formula 3, $R^3$ and/or $R^6$ independently denote a hydrogen atom, a crosslinking agent can be installed to form Formula 3 where $R^3$ and $R^6$ denote a crosslinking agent by a synthetic method described in Method 10:

[METHOD 10]

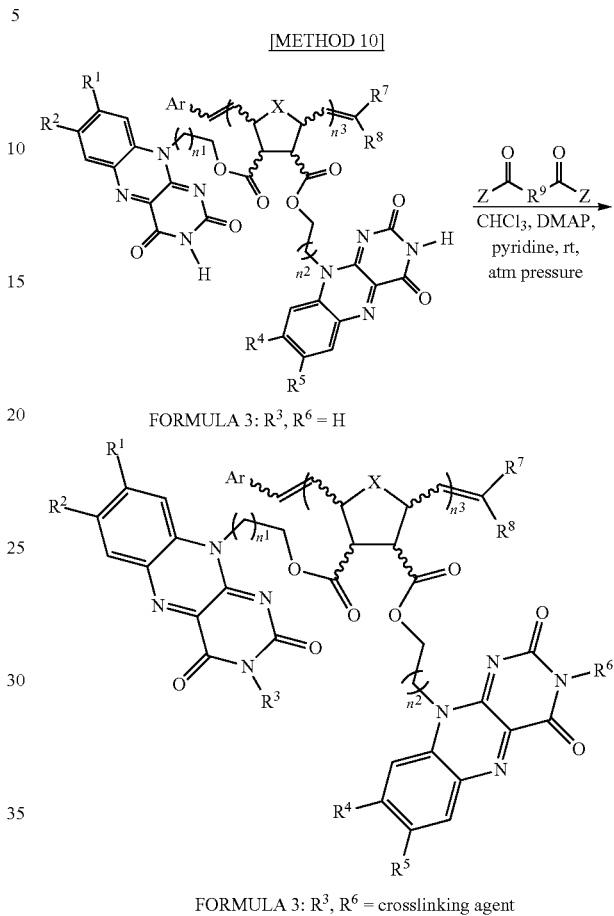

FORMULA 3: $R^3$, $R^6$ = H

FORMULA 3: $R^3$, $R^6$ = crosslinking agent

In Method 10, $R^1$, $R^2$, $R^4$, $R^5$, $R^7$, and $R^8$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a crosslinking agent installed by the conditions described in Method 10 (including but not limited to ester, amide, alkyl, aryl, or any polymer thereof). $R^9$ denotes an alkyl chain such as but not limited to ethyl, propyl, butyl, pentyl, or hexyl, an aromatic or heteroaromatic group such as but not limited to phenyl, biphenyl, thiophene, or pyrrole. X denotes either a carbon or oxygen atom. Here $n^1$ and $n^2$ each denote independently a number of repeat units ranging from 0 to 6. The repeat structure described by $n^3$ is any number of units ranging from 1 to 1000. Ar denotes the end group that is defined from the ring-opening polymerization catalyst that includes, but is not limited to, phenyl, tolyl, biphenyl or alkenyl.

The connectivity of the polymer chain is one of a homopolymer, a block copolymer, a gradient copolymer, an alternating copolymer, a semi-random copolymer, or a random copolymer. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Dimethylamino pyridine (DMAP) acts as a catalyst in order to speed up the reaction rate by reversibly reacting with the norbornene-type electrophile. Pyridine acts as a base in order to remove any acidic protons from the reaction in order to allow it to proceed. The base can also be a number of organic bases including but not limited to triethylamine, aniline, indole, piperidine, pyrimidine, pyrrolidine, pyrrole, imidazole, 4-diazabicyclo[2.2.2]octane, and 1,8-diazobicyclo[5.4.0]undec-7-ene. The temperature can be anywhere between −20 and 50 degrees Celsius and the pressure can be anywhere between 0.5 and 5 atmospheres.

Additionally, the compound in Formula 1 could be copolymerized with another ring-opening metathesis compound to form the compound described in Formula 5A/B having improved morphology, charge transport, electronic transport and/or stability:

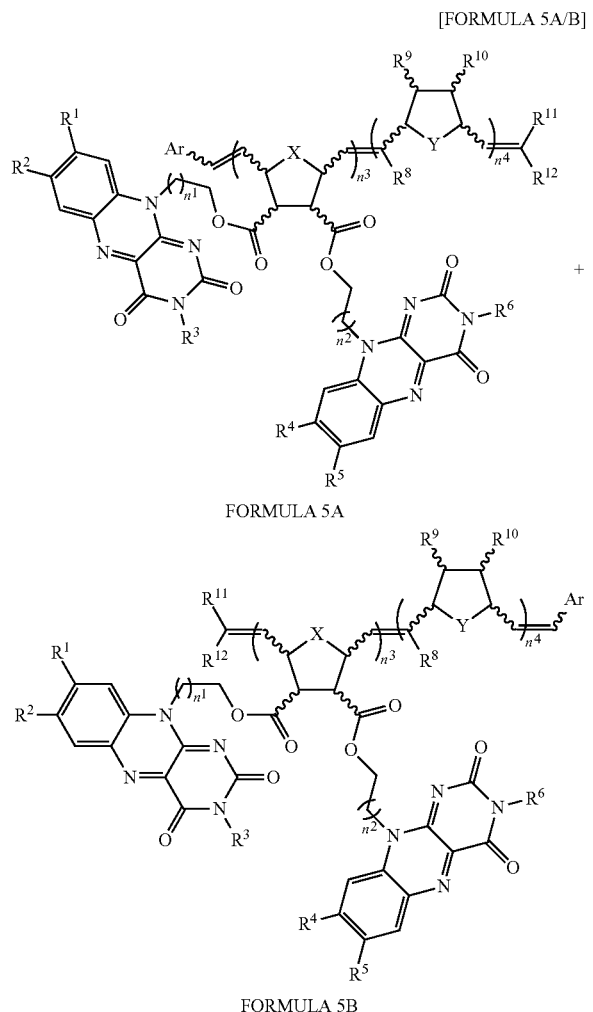

FORMULA 5A

FORMULA 5B

In Formula 5A/B, $R^1$, $R^2$, $R^4$, $R^5$, $R^8$, $R^{11}$, and $R^{12}$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). $R^9$ and $R^{19}$ each denote independently a hydrogen atom, alkyl group (including but not limited to methyl, ethyl, propyl, isopropyl, butyl), a polyether chain to improve ionic conductivity (including but not limited to a polyethylene glycol chain with a degree of polymerization less than or equal to 10) or a conjugated polymer chain to improve electrical conductivity (including but not limited to polyphenyl or polythiophene). X and Y each denote independently either a carbon or oxygen atom. Here $n^1$ and $n^2$ each denote independently a number of repeat units ranging from 0 to 6. The repeat structure described by $n^3$ and $n^4$ are, independently, any number of units ranging from 1 to 1000. Ar denotes the end group that is defined from the ring-opening polymerization catalyst that includes, but is not limited to, phenyl, tolyl, biphenyl or alkenyl.

By making slight changes to the polymerization conditions, the connectivity of the polymer may be favoured to be either toward Formula 5A or Formula 5B. The connectivity of the polymer chain can also be that of a homopolymer, block copolymer, gradient copolymer, alternating copolymer, semi-random copolymer, or random copolymer.

Formula 5A/B can be synthesized by polymerizing Formula 1 with another norbornene based ring opening metathesis monomer with appropriate functionality as described by Method 10.

[METHOD 10]

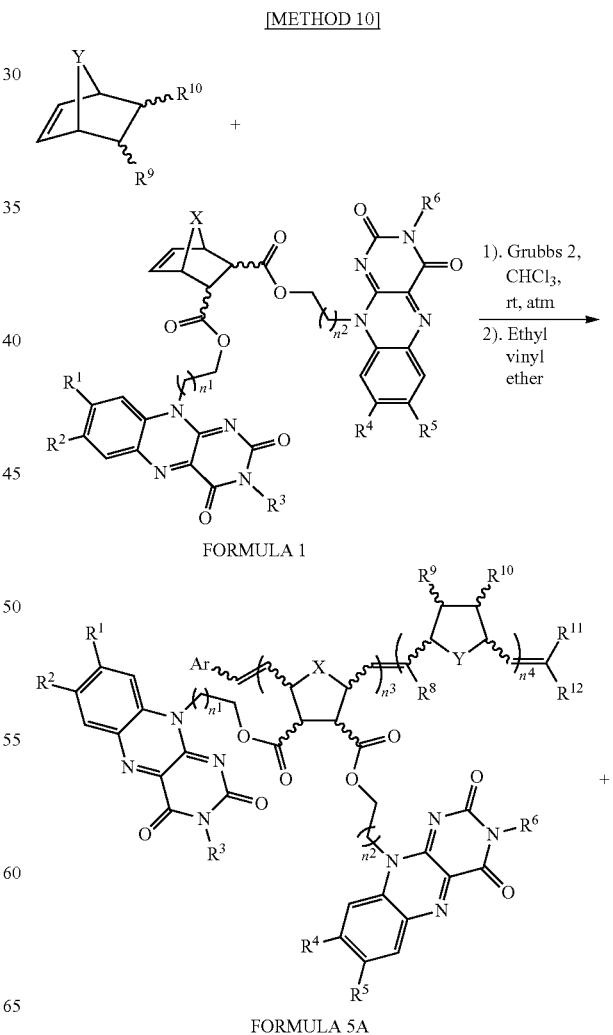

FORMULA 1

FORMULA 5A

-continued

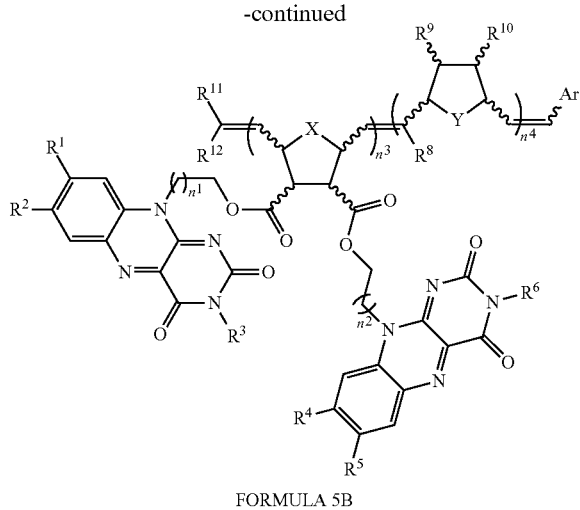

FORMULA 5B

In Method 10, $R^1$, $R^2$, $R^4$, $R^5$, $R^8$, $R^{11}$, and $R^{12}$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). $R^9$ and $R^{19}$ each denote independently a hydrogen atom, alkyl group (including but not limited to methyl, ethyl, propyl, isopropyl, butyl), a polyether chain to improve ionic conductivity (including but not limited to a polyethylene glycol chain with a degree of polymerization less than or equal to 10) or a conjugated polymer chain to improve electrical conductivity (including but not limited to polyphenyl or polythiophene). X and Y each denote independently either a carbon or oxygen atom. Here $n^1$ and $n^2$ each denote independently a number of repeat units ranging from 0 to 6. The repeat structure described by $n^3$ and $n^4$ are, independently, any number of units ranging from 1 to 1000. Ar denotes the end group that is defined from the ring-opening polymerization catalyst that includes, but is not limited to, phenyl, tolyl, biphenyl or alkenyl.

The connectivity of the polymer chain is one of a homopolymer, a block copolymer, a gradient copolymer, an alternating copolymer, a semi-random copolymer, or a random copolymer. The Grubbs 2 catalyst is a ring-opening metathesis catalyst, also referred to as an olefin metathesis catalyst, that is used to ring-open the norbornene based cyclic alkene and sequentially add monomer units to the growing chain in an olefin metathesis fashion in a controlled or uncontrolled manner. Here, controlled or uncontrolled refer to the ability to control, or not, the molecular weight or dispersity of the molecular weights of the resultant polymer. This Grubbs 2 catalyst can be substituted for any ring-opening metathesis catalyst that can include, but is not limited to, ruthenium carbene type catalysts such as Grubbs 1, Grubbs 3 or molybdenum or tungsten alkylidene type Schrock catalysts provided that they do not interfere or destroy the functionality on the monomer chains. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Ethyl vinyl ether is the terminating or end-capping reagent that acts to remove the catalyst from the growing polymer chain and replace it with an alkene with the appropriate substitutions $R^{11}$ and $R^{12}$. This terminating agent can be replaced with any reactive alkene that will remove the catalyst from the chain, terminating the polymerization and install the above mentioned end groups such as, but not limited to, propyl vinyl ether, butyl vinyl ether and benzyl vinyl ether.

The temperature can be anywhere between −20 and 50 degrees Celsius and the pressure can be anywhere between 0.5 and 5 atmospheres. The order of addition and the concentration of each monomer with respect to one another can be varied in order to adjust the connectivity or tendency to form more or less of Formula 5A and Formula 5B.

Method 10 can also produce cyclic polymers as a result of back-biting side reaction of the catalyst giving compounds with the structure described in Formula 6:

[FORMULA 6]

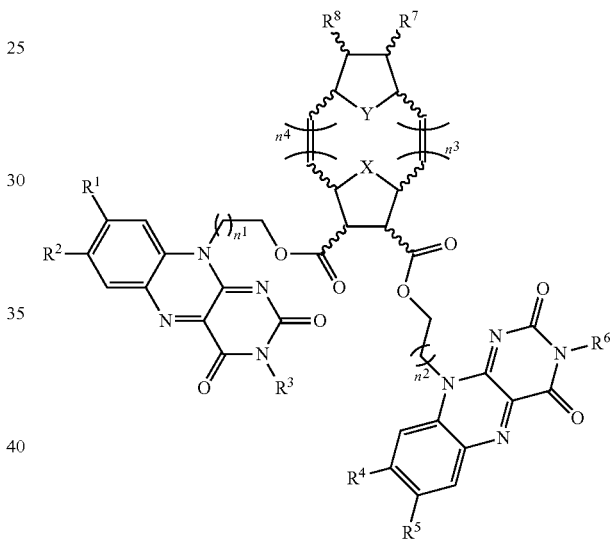

In Formula 6, $R^1$, $R^2$, $R^4$, and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). $R^7$ and $R^8$ each denote independently a hydrogen atom, alkyl group (including but not limited to methyl, ethyl, propyl, isopropyl, butyl), a polyether chain to improve ionic conductivity (including but not limited to a polyethylene glycol chain with a degree of polymerization less than or equal to 10) or a conjugated polymer chain to improve electrical conductivity (including but not limited to polyphenyl or polythiophene). X and Y each denote independently either a carbon or oxygen atom. Here $n^1$ and $n^2$ each denote independently a number of repeat units ranging from 0 to 6. The repeat structure described by $n^3$ and $n^4$ are, independently, any number of units ranging from 1 to 1000.

The connectivity of the polymer chain can also be that of a homopolymer, block copolymer, gradient copolymer, alternating copolymer, semi-random copolymer, or random copolymer.

In another aspect, the present disclosure provides an electroactive material that can be synthesized by polymerizing the compound described in Formula 2 to form an electroactive polymer with the repeat structure described in Formula 7:

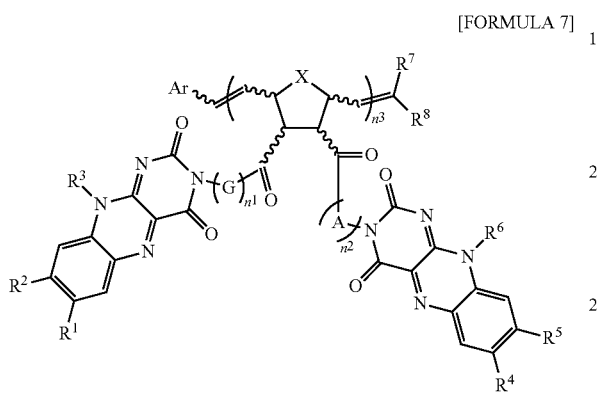

[FORMULA 7]

In Formula 7, $R^1$, $R^2$, $R^4$, $R^5$, $R^7$, and $R^8$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). X denotes either a carbon or oxygen atom. A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. The repeat structure described by $n^3$ is any number of units ranging from 1 to 1000. Ar denotes the end group that is defined from the ring-opening polymerization catalyst that includes, but is not limited to, phenyl, tolyl, biphenyl or alkenyl.

The connectivity of the polymer chain is one of a homopolymer, a block copolymer, a gradient copolymer, an alternating copolymer, a semi-random copolymer, or a random copolymer.

Formula 7 can be synthesized by subjecting Formula 2 to ring-opening metathesis polymerization conditions as described in Method 11:

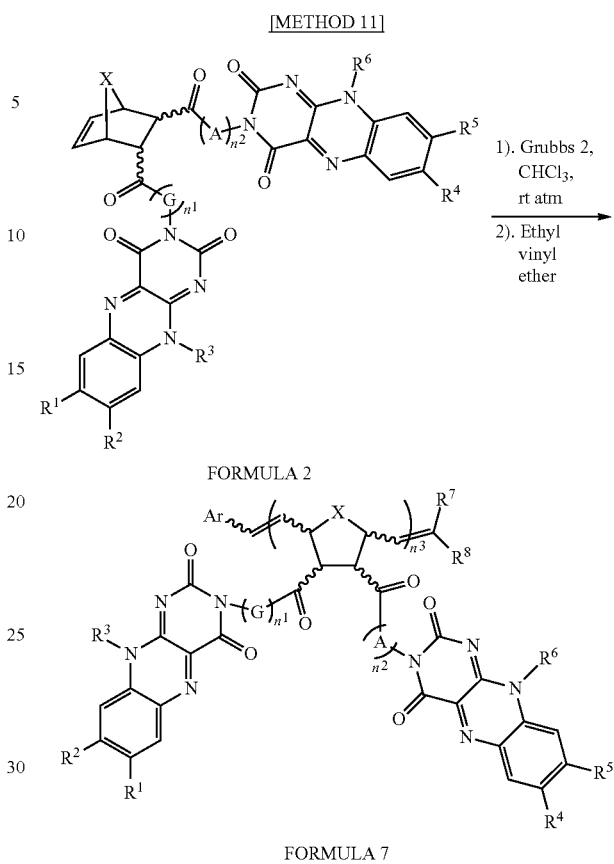

[METHOD 11]

1). Grubbs 2, CHCl$_3$, rt atm
2). Ethyl vinyl ether

FORMULA 2

FORMULA 7

In Formula 7, $R^1$, $R^2$, $R^4$, $R^5$, $R^7$, and $R^8$ each denote independently a hydrogen atom, alkyl group (including but not limited to methyl, ethyl, propyl, isopropyl, butyl), cyano group, nitro group, halogen, aromatic group or heteroaromatic group $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). X denotes either a carbon or oxygen atom. A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. The repeat structure described by $n^3$ is any number of units ranging from 1 to 1000. Ar denotes the end group that is defined from the ring-opening polymerization catalyst that includes, but is not limited to, phenyl, tolyl, biphenyl or alkenyl.

The connectivity of the polymer chain is one of a homopolymer, a block copolymer, a gradient copolymer, an alternating copolymer, a semi-random copolymer, or a random copolymer. The Grubbs 2 catalyst is a ring-opening metathesis catalyst, also referred to as an olefin metathesis catalyst, that is used to ring-open the norbornene based cyclic alkene and sequentially add monomer units to the growing chain in an olefin metathesis fashion in a controlled or uncontrolled manner. Here, controlled or uncontrolled refer to the ability to control, or not, the molecular weight or dispersity of the molecular weights of the resultant polymer. This Grubbs 2 catalyst can be substituted for any ring-opening metathesis catalyst that can include, but is not In the case where in Formula 7, $R^3$ and/or $R^6$ independently denote a crosslinking precursor such as, but not limited to, an alcohol group, amine or sulfide, a crosslinking agent can be installed to form Formula 7 where $R^3$ and $R^6$ denote a crosslinking agent by a synthetic method described in Method 12:

[METHOD 12]

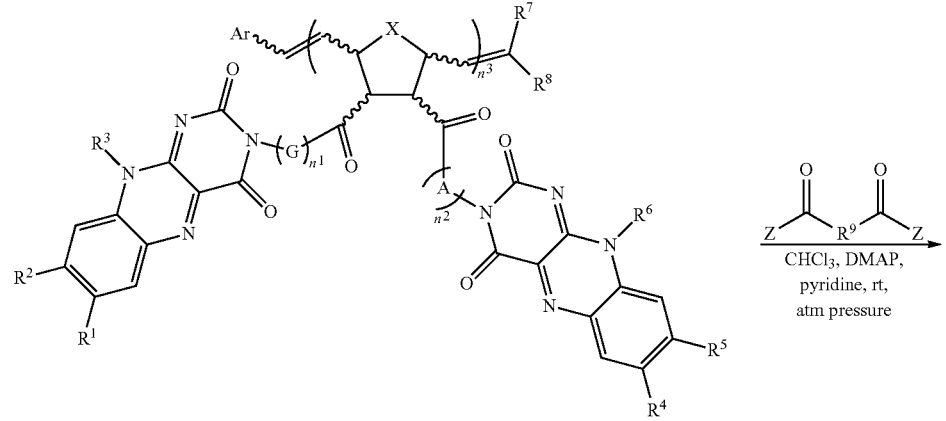

FORMULA 7: $R^3, R^6$ = crosslinking precursor

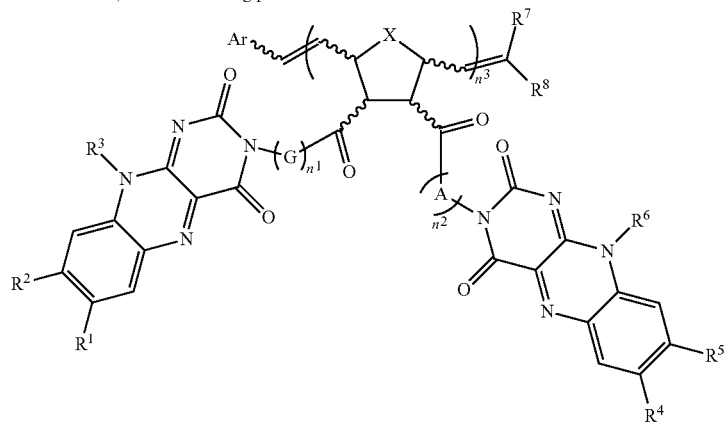

FORMULA 7: $R^3, R^6$ = crosslinking agent limited to, ruthenium carbene type catalysts such as Grubbs 1, Grubbs 3 or molybdenum or tungsten alkylidene type Schrock catalysts provided that they do not interfere or destroy the functionality on the monomer chains.

CHCl$_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above. Ethyl vinyl ether is the terminating or end-capping reagent that acts to remove the catalyst from the growing polymer chain and replace it with an alkene with the appropriate substitutions $R^7$ and $R^8$. This terminating agent can be replaced with any reactive alkene that will remove the catalyst from the chain, terminating the polymerization and install the above mentioned end groups such as, but not limited to, propyl vinyl ether, butyl vinyl ether and benzyl vinyl ether. The temperature can be anywhere between −20 and 50 degrees Celsius and the pressure can be anywhere between 0.5 and 5 atmospheres.

In Method 12, $R^1$, $R^2$, $R^4$, $R^5$, $R^7$, and $R^8$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). $R^9$ denotes an alkyl chain such as but not limited to ethyl, propyl, butyl, pentyl, or hexyl, an aromatic or heteroaromatic group such as but not limited to phenyl, biphenyl, thiophene, or pyrrole. X denotes either a carbon or oxygen atom. A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. The repeat structure described by $n^3$ is any number of units ranging from 1 to 1000. Ar denotes the end group that is defined from the ring-opening polymerization catalyst that includes, but is not limited to, phenyl, tolyl, biphenyl or alkenyl.

The connectivity of the polymer chain is one of a homopolymer, a block copolymer, a gradient copolymer, an alternating copolymer, a semi-random copolymer, or a random copolymer. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above.

Dimethylamino pyridine (DMAP) acts as a catalyst in order to speed up the reaction rate by reversibly reacting with the norbornene-type electrophile. Pyridine acts as a base in order to remove any acidic protons from the reaction in order to allow it to proceed. The base can also be a number of organic bases including but not limited to triethylamine, aniline, indole, piperidine, pyrimidine, pyrrolidine, pyrrole, imidazole, 4-diazabicyclo[2.2.2]octane, and 1,8-diazobicyclo[5.4.0]undec-7-ene. The temperature can be anywhere between −20 and 50 degrees Celsius and the pressure can be anywhere between 0.5 and 5 atmospheres.

Additionally, the compound in Formula 2 could be copolymerized with another ring-opening metathesis compound to form the compound described in Formula 8A/B having improved morphology, charge transport, electronic transport and/or stability:

[FORMULA 8A/B]

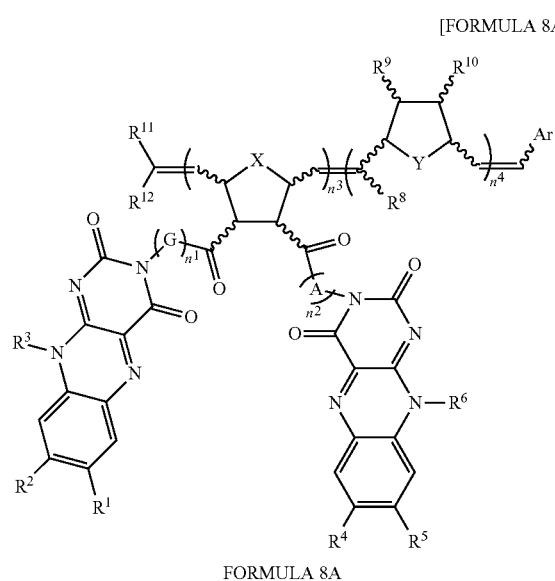

FORMULA 8A

+

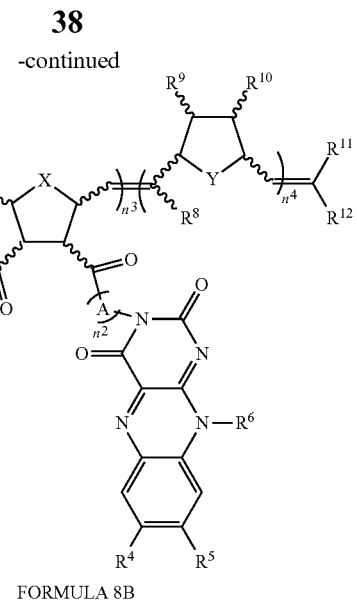

FORMULA 8B

In Formula 8A/B, $R^1$, $R^2$, $R^4$, $R^5$, $R^8$, $R^{11}$, and $R^{12}$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). $R^9$ and $R^{10}$ each denote independently a hydrogen atom, alkyl group (including but not limited to methyl, ethyl, propyl, isopropyl, butyl), a polyether chain to improve ionic conductivity (including but not limited to a polyethylene glycol chain with a degree of polymerization less than or equal to 10) or a conjugated polymer chain (including but not limited to polyphenyl or polythiophene). X and Y each denote independently either a carbon or oxygen atom. A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. The repeat structure described by $n^3$ and $n^4$ are, independently, any number of units ranging from 1 to 1000. Ar denotes the end group that is defined from the ring-opening polymerization catalyst that includes, but is not limited to, phenyl, tolyl, biphenyl or alkenyl.

The connectivity of the polymer chain can also be that of a homopolymer, block copolymer, gradient copolymer, alternating copolymer, semi-random copolymer, or random copolymer.

Formula 8A/B can be synthesized by polymerizing Formula 2 with another norbornene based ring opening metathesis monomer with appropriate functionality as described by Method 13:

[METHOD 13]

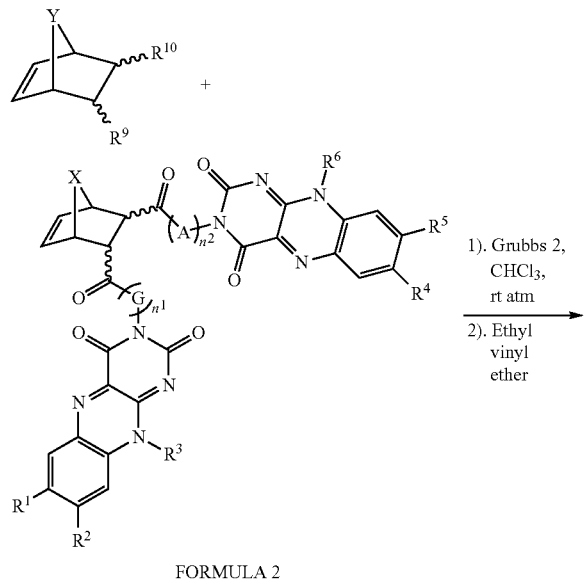

FORMULA 2

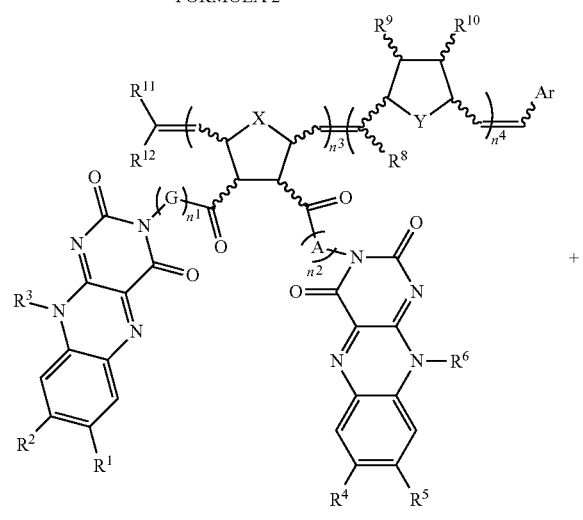

FORMULA 8A

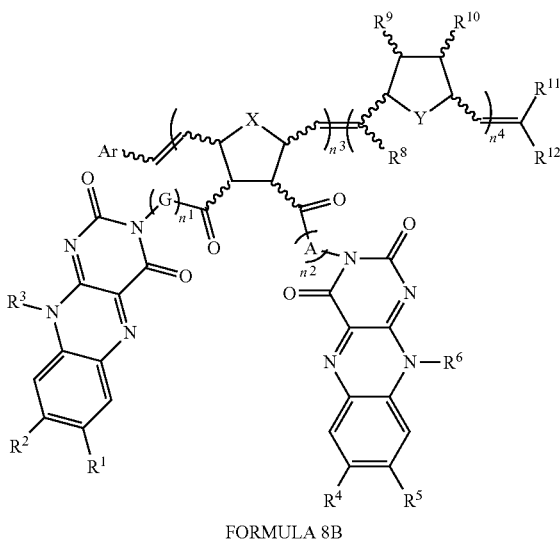

FORMULA 8B

In Method 13, $R^1$, $R^2$, $R^4$, $R^5$, $R^8$, $R^{11}$, and $R^{12}$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), alcohol group (including but not limited to methanol, ethanol, propanol, isopropanol, butanol) aromatic group, heteroaromatic group, ester group or crosslinking agent (including but not limited to ester, amide, alkyl, aryl, or any polymer thereof). $R^9$ and $R^{19}$ each denote independently a hydrogen atom, alkyl group (including but not limited to methyl, ethyl, propyl, isopropyl, butyl), a polyether chain to improve ionic conductivity (including but not limited to a polyethylene glycol chain with a degree of polymerization less than or equal to 10) or a conjugated polymer chain to improve electronic conductivity (including but not limited to polyphenyl or polythiophene). X and Y each denote independently either a carbon or oxygen atom.

A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. The repeat structure described by $n^3$ and $n^4$ are, independently, any number of units ranging from 1 to 1000. Ar denotes the end group that is defined from the ring-opening polymerization catalyst that includes, but is not limited to, phenyl, tolyl, biphenyl or alkenyl. The Grubbs 2 catalyst is a ring-opening metathesis catalyst, also referred to as a olefin metathesis catalyst, that is used to ring-open the norbornene based cyclic alkene and sequentially add monomer units to the growing chain in an olefin metathesis fashion in a controlled or uncontrolled manner. Here, controlled or uncontrolled refer to the ability to control, or not, the molecular weight or dispersity of the molecular weights of the resultant polymer described above in Formula 8A/B.

This Grubbs 2 catalyst can be substituted for any ring-opening metathesis catalyst that can include, but is not limited to, ruthenium carbene type catalysts such as Grubbs 1, Grubbs 3 or molybdenum or tungsten alkylidene type Schrock catalysts provided that they do not interfere or destroy the functionality on the monomer chains. $CHCl_3$ acts as the solvent and allows the reagents to react together without reacting itself with any of the reagents. The solvent could also be, but is not limited to, dichloromethane, ether, ethyl acetate, dimethyl formamide, acetonitrile and any combination of the above.

Ethyl vinyl ether is the terminating or end-capping reagent that acts to remove the catalyst from the growing polymer chain and replace it with an alkene with the appropriate substitutions $R^{11}$ and $R^{12}$. This terminating agent can be replaced with any reactive alkene that will remove the catalyst from the chain, terminating the polymerization and install the above mentioned end groups such as, but not limited to, propyl vinyl ether, butyl vinyl ether and benzyl vinyl ether. The temperature can be anywhere between −20 and 50 degrees Celsius and the pressure can be anywhere between 0.5 and 5 atmospheres. The order of addition and the concentration of each monomer with respect to one another can be varied in order to adjust the connectivity or tendency to form more or less of Formula 8A and Formula 8B. The connectivity of the polymer chain can also be that of a homopolymer, block copolymer, gradient copolymer, alternating copolymer, semi-random copolymer, or random copolymer.

Method 13 can also produce cyclic polymers as a result of back-biting of the catalyst giving compounds with the structure described in Formula 9:

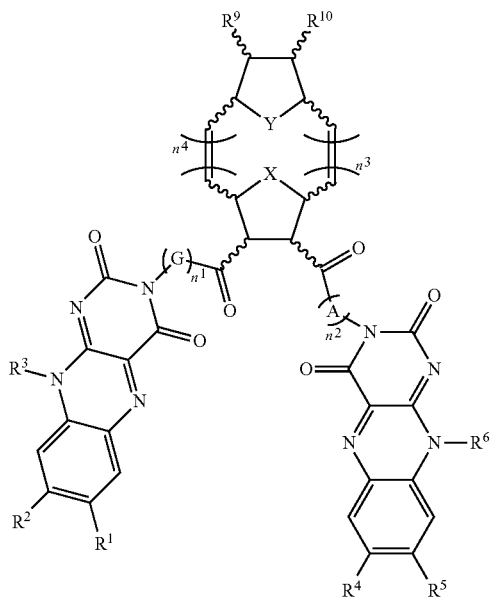

[FORMULA 9]

In Formula 9, $R^1$, $R^2$, $R^4$, and $R^5$ each denote independently a hydrogen atom, alkyl group (including but not limited to methyl, ethyl, propyl, isopropyl, butyl), cyano group, nitro group, halogen, aromatic group or heteroaromatic group. $R^3$ and $R^6$ each denote independently a hydrogen atom, alkyl group (including but not limited to methyl, ethyl, propyl, isopropyl, butyl), aromatic group, heteroaromatic group or crosslinking agent (including but not limited to ester, amide, alkyl, aryl, or any polymer thereof). $R^9$ and $R^{19}$ each denote independently a hydrogen atom, alkyl group (including but not limited to methyl, ethyl, propyl, isopropyl, butyl), a polyether chain to improve ionic conductivity (including but not limited to a polyethylene glycol chain with a degree of polymerization less than or equal to 10) or a conjugated polymer chain to improve electronic conductivity (including but not limited to polyphenyl or polythiophene).

X and Y each denote independently either a carbon or oxygen atom. A and G each denote independently a carbon based aliphatic chain that has an end functional group such as but not limited to hydroxyl and amino that can be used to link the flavin unit through the diimide nitrogen to the norbornene based polymerization unit. Here $n^1$ and $n^2$ each denote independently a number of repeat units of the above mentioned carbon chain A and G ranging from 0 to 6 in length. The repeat structure described by $n^3$ and $n^4$ are, independently, any number of units ranging from 1 to 1000.

The connectivity of the polymer chain can also be that of a homopolymer, block copolymer, gradient copolymer, alternating copolymer, semi-random copolymer, or random copolymer.

Example 1

Confirmation of Chemical Structure

The chemical structures of specific examples of Formula 1 and Formula 3 were characterized by the following methods. Fourier transform infrared (FT-IR) spectroscopy was carried out using a Perkin Elmer Spectrum 100 FT-IR spectrometer equipped with a 10-bounce diamond/ZnSe ATR accessory. Optical absorption spectroscopy was performed using a Varian Cary 5000 ultraviolet-visible-near infrared (UV-Vis-NIR) spectrophotometer. Fluorescence spectra were collected using a Photon Technology International (PTI) QuantaMaster 40-F NA spectrofluorometer with a photomultiplier detector and a xenon arc lamp source. Proton nuclear magnetic resonance spectroscopy (NMR) was carried out on a Bruker Avance III 400 operating at 400 MHz. Chemical shifts are reported in ppm at room temperature using the solvent peak of $CDCl_3$ or $d_6$-dimethylsulfoxide (DMSO) at 7.26 or 2.50 ppm respectively. Mass spectrometry was performed using a JOEL AccuTOF JMS-T1000LC mass spectrometer equipped with a direct analysis in real time (DART) ion source or an Agilient 6528 Q-TOF (time-of-flight) mass spectrometer. The thermal properties of specific examples of Formula 3 were investigated Thermogravimetric analysis (TGA) and differential scanning calorimetry (DSC) were performed on a SDT Q600 V8.3 Build 101 at a heating rate of 5° C./min under nitrogen in order to determine their performance at high temperature.

Example 2

Electrochemical Measurements

Electrochemical measurements were performed in order to determine the applicability of specific examples of Formula 1 and Formula 3 towards lithium-ion batteries. All electrolyte solvents and salts were purchased from Sigma-Aldrich and used as received. All electrochemical measurements were recorded in an argon filled glovebox (mBraun) and performed using a Biologic SP-200.
Potentiostat/Galvanostat/Frequency Response Analysis (FRA) Frequency response measurements were performed on electrodes made by the procedures outlined below on specific examples of Formula 3 in order to gain insight on the response of the electrode to alternating current and the resistances associated with the electrode. Impedance spectra were measured with an excitation amplitude of 10 mV from a frequency range of 150 kHz-0.1 Hz. Films were cast by dissolving 35 mg of Formula 3 with $R^1$, $R^2$, $R^3$, $R^4$, $R^5$, and $R^6$ being methyl groups, $R^7$ and $R^8$ being hydrogens, X being a methylene group, $n^1$ and $n^2$ are both equal to 1, $n^3$ being between 1 and 1000, Ar being phenyl, and the stereochemistry on the pendant ester groups such that they adopt an endo, exo conformation relative to each other in a racemic mixture, hereby referred to as 2, and 50 mg of carbon black (CB, carbon black, acetylene purchased from Alfa-Aesar) in 17 mL of chloroform and stirring vigorously overnight. The solvent was then removed under vacuum and 15 mg of polyvinylidene difluoride (PVdF, Sigma-Aldrich) powder was added, then the mixture was sonicated in 1.66 mL of N-methyl pyrrolidone (NMP) for 1 hour, stirring every 15 minutes to improve homogenization. In order to prepare the films with nanoparticles, nanoparticles were first made by precipitation of a 5 mg $mL^{-1}$ chloroform solution of 2 into a rapidly stirring beaker of methanol. The nanoparticles of 2, CB and PVDF were then mixed together in a ratio of 35:50:15 in N-methyl pyrrolidone (NMP) at a concentration of 60 mg $mL^{-1}$, sonicated for 1 hour, stirring every 15 minutes to homogenize. The films were then cast as described above. 2032 type coin cells were purchased from MTI Corporation. A copper foil (McMaster-Carr) was used as the anodic current collector, a lithium foil with a diameter of 16 mm was used as the anode, and a Celgard lithium-ion battery separator film as the separator with a diameter of 19 mm. A stainless steel spacer and a stainless steel spring were placed on top of the cathode material prior to sealing. An electrode punch (Design Prove Machines (DPM) Solutions Inc.) was used to cut electrodes of a certain diameter and a coin cell press (BT Innovations) was used to hermetically seal the cells.

Example 3

Electrode Characterization

The morphology of the electrode films mentioned above were examined using scanning electron microscopy (SEM) (Hitachi S-5200 SEM) and atomic force microscopy (AFM) was carried out using a Bruker Dimension Icon Atomic Force Microscope in tapping mode. Profilometry was performed using a KLA-Tencore P16+ profilometer with a 0.5 mg force setting and a scanning length of 2.5 microns. Powder X-ray diffraction (PXRD) was performed on a Rigaku MiniFlex 600 X-ray Diffractometer. These measurements were performed in order to assess electrode fabrication and degradation upon charging and discharging.

Example 4

Computational Details:
Geometry Optimizations were Performed Using the Gaussian 09 Software Suite at the B3LYP Level of Theory and the Standard TZVP Basis Set.

Geometry optimizations were used to determine the amount of structural change associated with charging and discharging the electroactive materials in Formulas 3 to 9. This was used to assess the stability to expect from the compounds and was therefore used to improve upon the structures of the electroactive materials. With more structural change upon charging and discharging, the less stable an electroactive material. By changing the connectivity and lengths of the spacer chains, the structure can be tuned in order to give better or worse stability. The geometry optimizations also give information about the voltages at which to expect the final battery to be with different structural variations. This is used in order to further optimize the structures in Formulas 3 to 9. See [Hernández-Burgos, K., Rodríguez-Calero, G. G., Zhou, W., Burkhardt, S. E., & Abruña, H. D. (2013). Increasing the Gravimetric Energy Density of Organic Based Secondary Battery Cathodes Using Small Radius Cations (Li+ and Mg 2+). *Journal of the American Chemical Society*, 135(39), 14532-14535] for details on computational modeling of charged organics for batteries.

Test Example

For a test example, we describe the synthesis, characterization and performance of a lithium-ion battery with the structure described in Formula 1:

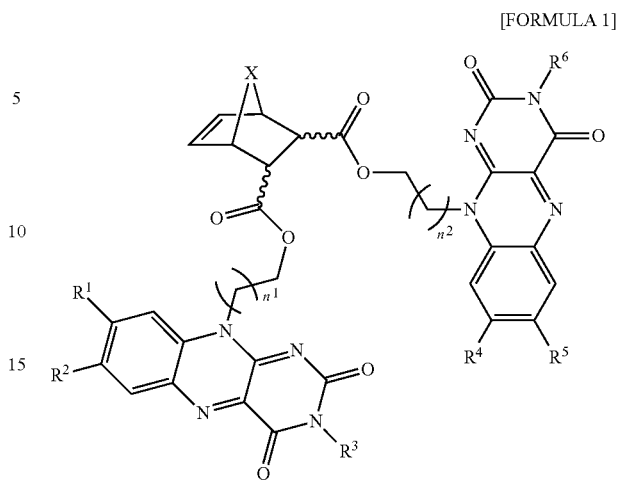

[FORMULA 1]

In this test example of Formula 1, $R^1$, $R^2$, $R^3$, $R^4$, $R^5$, and $R^6$ are methyl groups, X is a methylene group and $n^1$ and $n^2$ are both equal to 1. The stereochemistry on the pendant ester groups is such that they adopt an endo, exo conformation relative to each other in a racemic mixture. Hereafter, this specific example is referred to as compound 1.

We targeted the radical-free ring opening metathesis polymerization (ROMP) using a norbornene based monomer where two flavin units are attached through endo, exo ester groups. The endo, exo diacid chloride was chosen because of the decreased charge repulsion between pendant units. Following the scheme in Method 1, coupling the free alcohol on compound 1 described in to a norbornene diacid chloride using a basic catalyst, a base to remove the acid protons and a solvent, the compound described in Formula 1 was synthesized.

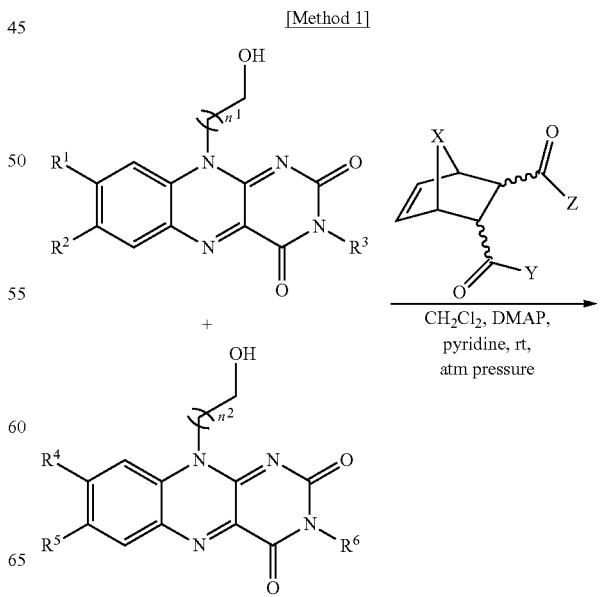

[Method 1]

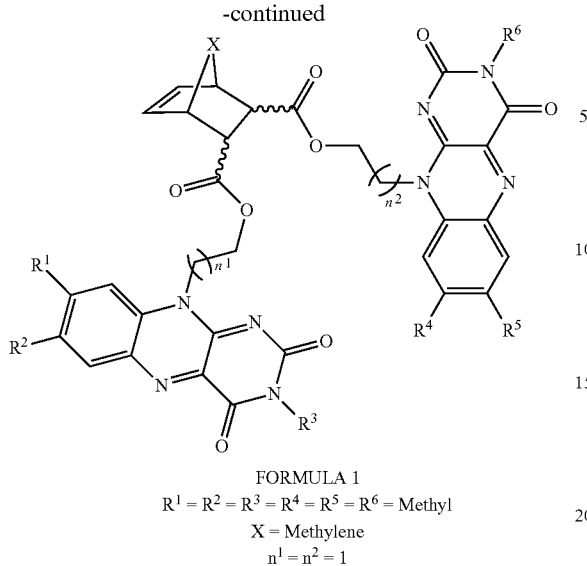

FORMULA 1
R$^1$ = R$^2$ = R$^3$ = R$^4$ = R$^5$ = R$^6$ = Methyl
X = Methylene
n$^1$ = n$^2$ = 1

Here described in this example of Method 1, Z and Y are chlorines and the stereochemistry of the ester groups on the norbornene unit are in endo, exo conformation and it exists as a racemic mixture. To a flame dried flask, 1 g (3.49 mmol) of 10-(2-hydroxyethyl)-7,8 dimethylbenzo[g]pteridine-2,4 (3H,10H)-dione and 3.42 g of Cs$_2$CO$_3$ (10.5 mmol) was suspended in 30 mL of dimethylformamide (DMF). To the suspension, 0.44 mL (6.99 mmol) of methyl iodide was added. The reaction was monitored by TLC (5:1 CH$_2$Cl$_2$: MeOH). Upon completion, the reaction was dumped into 0.1 M HCl$_{(aq)}$ and was washed 3 times with CH$_2$Cl$_2$. The aqueous layer was filtered and dried to yield 1 as a light yellow-brown product (0.72 g, 69%). $^1$H NMR (400 MHz, d$_6$-DMSO): 7.94 (s, 1H), 7.91 (s, 1H), 4.95 (t, J=6.0 Hz, 1H), 4.72 (t, J=6.1 Hz, 2H), 3.82 (q, J=6.0 Hz, 2H), 3.28 (s, 3H), 2.51 (s, 3H), 2.41 (s, 3H). HRMS (DART) m/s calculated for C$_{15}$H$_{17}$N$_4$O$_3$ [M+H]$^+$: 301.1295; found: 301.1298. The synthesis of 10-(2-hydroxyethyl)-7,8-dimethylbenzo[g]pteridine-2,4(3H,10H)-dione was performed according to Kino, K., Miyazawa, H. & Sugiyama, H. User-friendly Synthesis and Photoirradiation of a Flavin-linked Oligomer. *Genes and Environment* 29, 23-28 (2007).

Using Formula 1 with R$^1$, R$^2$, R$^3$, R$^4$, R$^5$, and R$^6$ being methyl groups, X being a methylene group and n$^1$ and n$^2$ are both equal to 1 with the stereochemistry on the pendant ester groups such that they adopt an endo, exo conformation relative to each other in a racemic mixture, referred to as 1, a specific example of Formula 3 was synthesized by Method 9.

[METHOD 9]

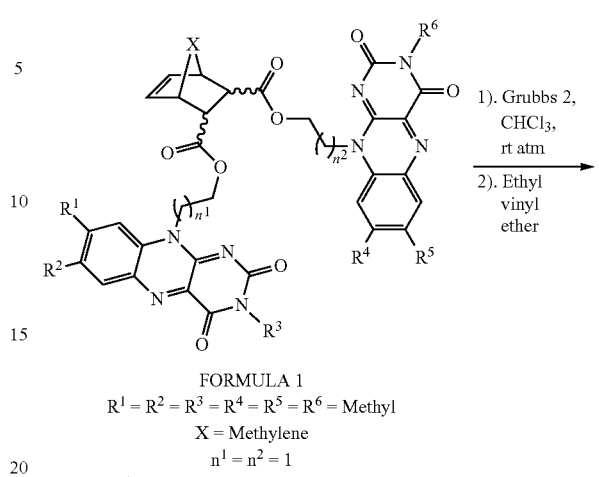

FORMULA 1
R$^1$ = R$^2$ = R$^3$ = R$^4$ = R$^5$ = R$^6$ = Methyl
X = Methylene
n$^1$ = n$^2$ = 1

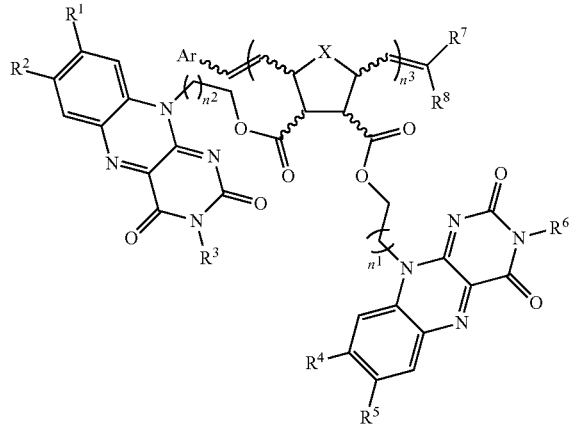

FORMULA 3
R$^1$ = R$^2$ = R$^3$ = R$^4$ = R$^5$ = R$^6$ = Methyl
R$^7$ = R$^8$ = H
X = Methylene
n$^1$ = n$^2$ = 1
n$^3$ = 1 to 1000
Ar = phenyl Here in this example, the ester groups on the norbornene unit are in an endo, exo conformation and the mixture is racemic. 1 (1.5 g, 2 mmol) and 20 mL of CHCl$_3$ were added to a flame dried flask. Afterwards, 17 mg (0.02 mmol) of Grubbs' 2$^{nd}$ generation catalyst was added and the solution was stirred at room temperature in the dark for 19 hours. The reaction was quenched with 0.96 mL (10 mmol) of ethyl vinyl ether dissolved in 7 mL of CHCl$_3$ and allowed to stir for another 5 hours. The resultant compound, Formula 3, was then precipitated in methanol twice, soxhlet extracted with methanol for 4 days and then dissolved in CHCl$_3$. The solvent was removed to yield a dark green solid (1.3 g, 84%). $^1$H NMR (400 MHz, CDCl$_3$): 7.76 (broad s, 4H), 4.91-4.37 (broad m, 9H), 3.28-2.82 (broad s, 8H), 2.48-1.74 (broad m, 17H).

Figure 5:
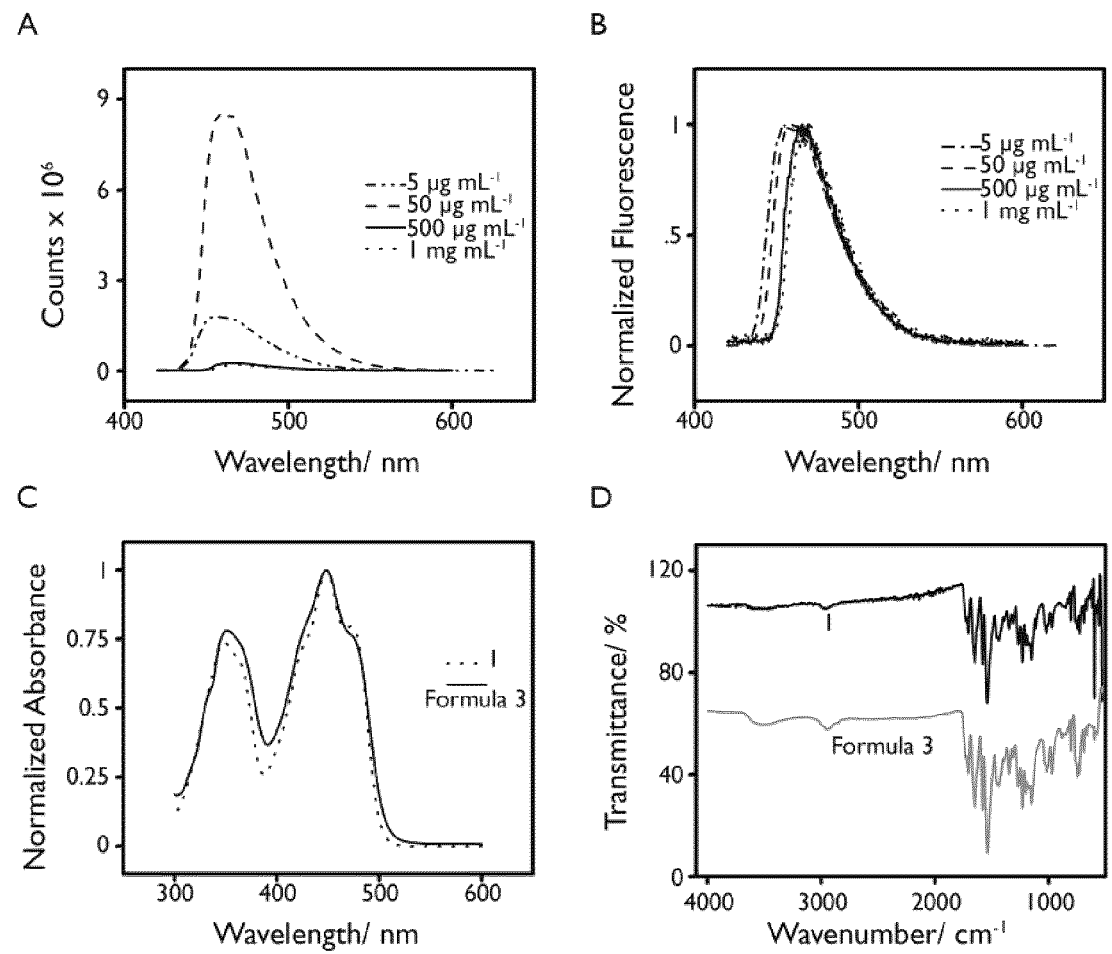
FIG. 5. (a,b) Fluorescence of Formula 3, (c) UV-Vis spectra, and (d) FTIR spectra of 1 and Formula 3.
Figure 6:
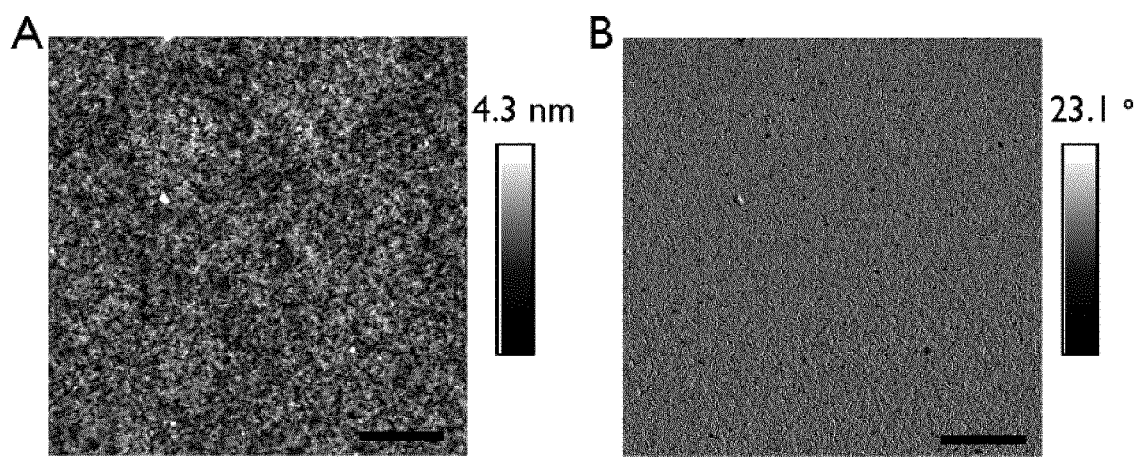
FIG. 6. AFM (a) height and (b) phase images of spuncast Formula 3 on glass slides. The scale bar is 1 μm.
Figure 15:
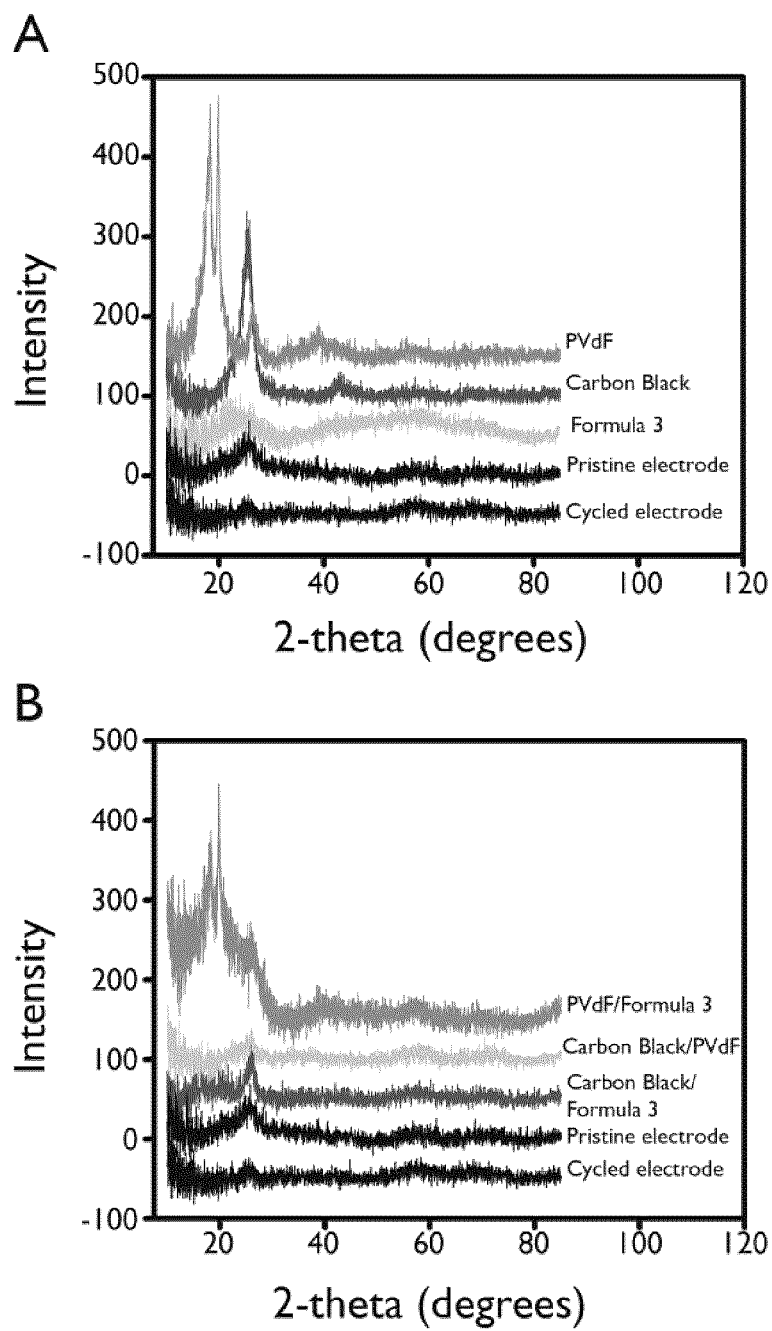
FIG. 15. Powder X-ray diffraction of (a) cycled and pristine electrodes compared to the individual components and (b) cycled and pristine electrodes compared to binary mixtures of the components.

Formula 3 is a dark green solid, highly fluorescent in dilute solutions, and only slightly soluble in dichloromethane or chloroform (FIG. 5). Formula 3 is solution processable, forming smooth, featureless films as observed by AFM (FIG. 6), indicating that the molecule of Formula 3 is amorphous (FIG. 6). The lack of crystallinity is also supported by PXRD (FIG. 15).

Polyflavin Characterization

Figure 7:
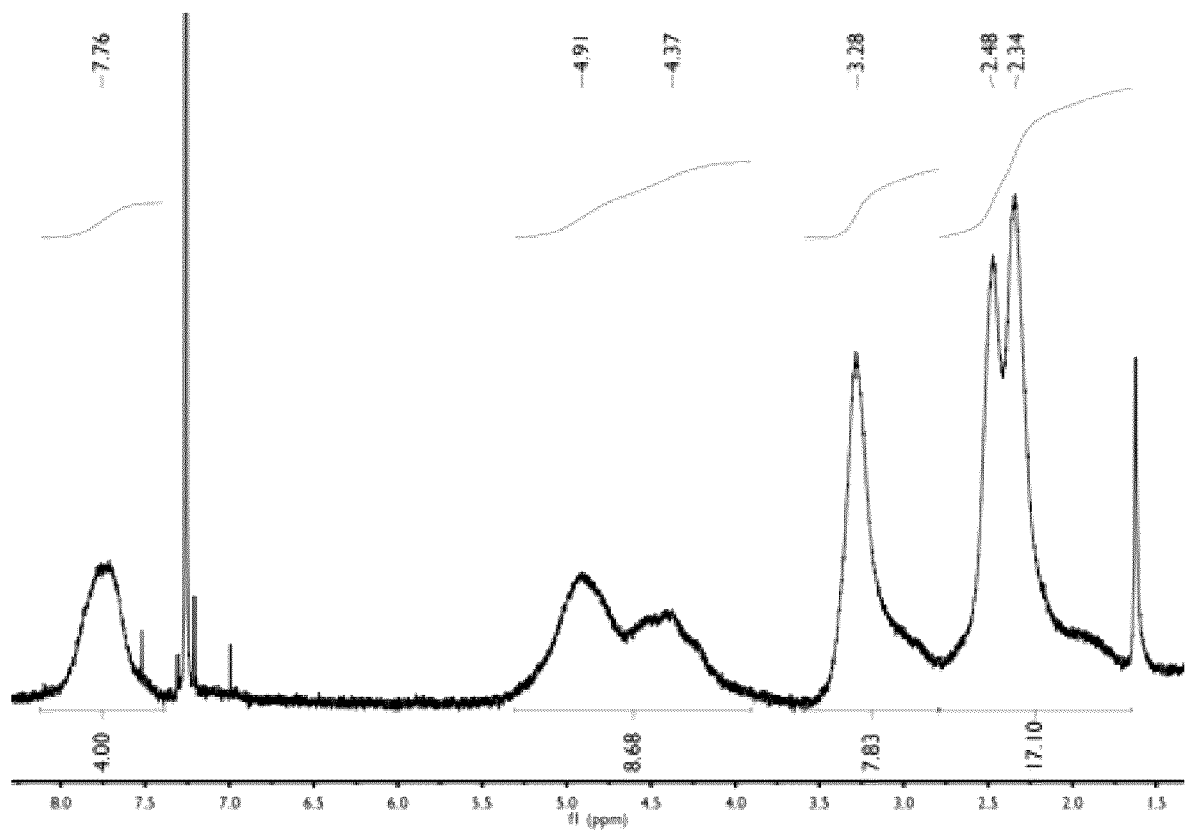
FIG. 7. Proton NMR spectra of Formula 3.

Formula 3 was difficult to characterize due to low solubility. The proton NMR spectra (FIG. 7) shows broad, low intensity peaks with the expected chemical shifts for a norbornene-based polymer. End group analysis to determine the degree of polymerization of Formula 3 was unsuccessful due to the low solubility and the overlapping end group peaks with those of the polymer backbone and pendant units. Attempts to characterize the Formula 3's molecular weight by light scattering and gel permeation chromatography (GPC) were unsuccessful due to aggregation even in dilute solutions. Although the insolubility of Formula 3 leads to problems with characterization, insolubility is a requirement for high performance in batteries since solubility is a main contribution to decreased capacity upon cycling for organic electrodes. The optical properties were probed by UV-vis spectroscopy (FIG. 5).

The spectra of Formula 3 and 1 both have two distinct maxima centered at 349 and 448 nm. The absorption spectrum of 1 also has a shoulder at 473 nm which does not appear in Formula 3. The FT-IR spectra of Formula 3 (FIG. 5) shows weak signals corresponding to the aliphatic C—H bonds below 3000 $cm^{-1}$, various carbonyl stretches in the range of 1750-1500 $cm^{-1}$ corresponding to the ester and diimide groups, along with various stretches in the fingerprint region. The FT-IR spectra of 1 is almost identical to Formula 3 due to their similar bonding motifs and structure.

Figure 8:
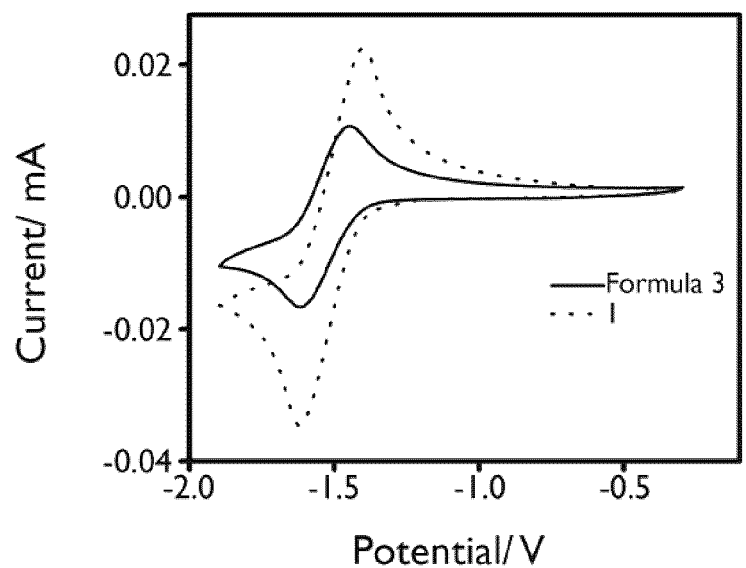
FIG. 8. CV at 100 mV/s of Formula 3 and 1 in 0.1 M $TBAPF_6$ dichloromethane in solution. The potential is referenced to $Fc/Fc^+$.

To determine if the polymerization affected electrochemistry, cyclic voltammetry (CV) was performed on 1 and Formula 3 separately in solution using 0.1 M tetrabutylammonium hexafluorophosphate ($TBAPF_6$) in dichloromethane at 100 mV $s^{-1}$ with a 10 mM concentration of the flavin unit (FIG. 8).

The redox wave centered at −1.50 V vs the ferrocene/ferrocenium ($Fc/Fc^+$) redox couple is not shifted between 1 and Formula 3 indicating that the polymerization did not modify the redox characteristics of the flavin unit. However, the magnitude of the peak current is decreased, which can be attributed to the lower diffusion rate of the redox units to the electrode due to the low diffusion coefficient of Formula 3.

Figure 9:
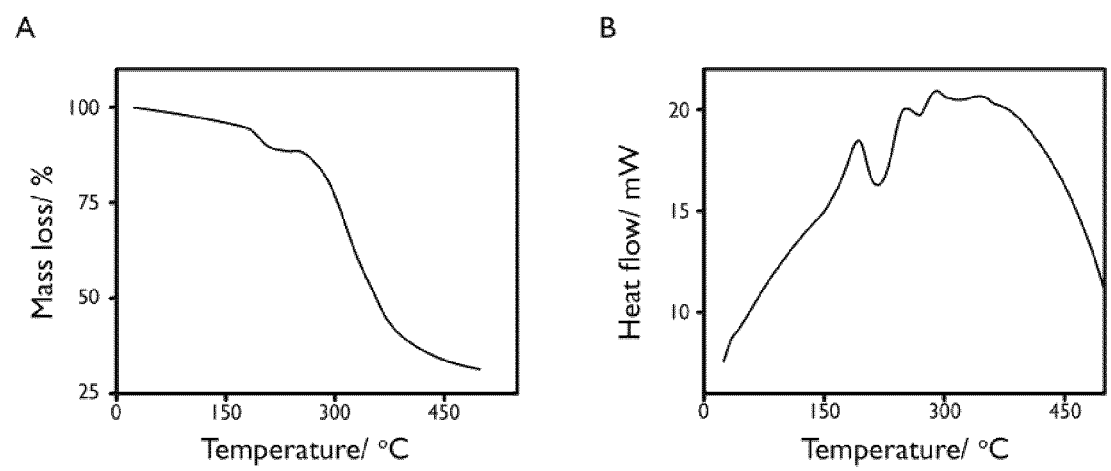
FIG. 9. (a) TGA and (b) DSC of Formula 3.

The thermal properties of Formula 3 were investigated using TGA and DSC (FIG. 9). Formula 3 is stable under heating until 170° C. Formula 3 does not have a glass transition or melting temperature before it decomposes.

Polyflavin Electrode Characterization

Figure 2:
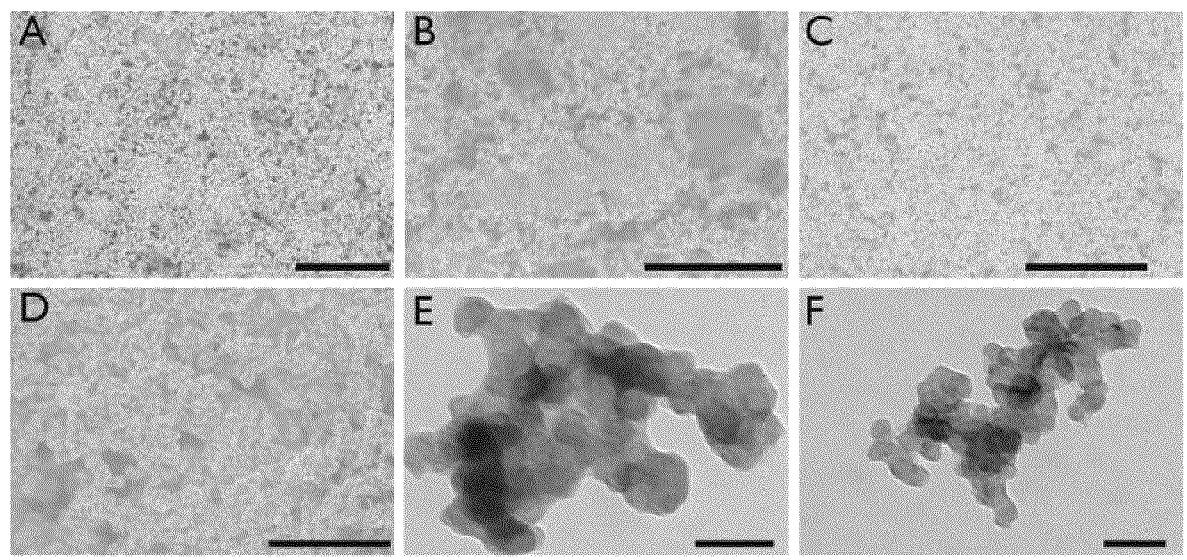
FIG. 2. SEM images of (a,b) films cast with prepared Formula 3 nanoparticles and (c,d) films cast by first dissolving Formula 3 in $CHCl_3$ with CB. Scale bars are 10 μm, 5 μm, 10 μm, and 2 μm respectively. TEM images of (e) Formula 3 CB hybrids and (f) CB. Scale bars are 100 nm.
Figure 10:
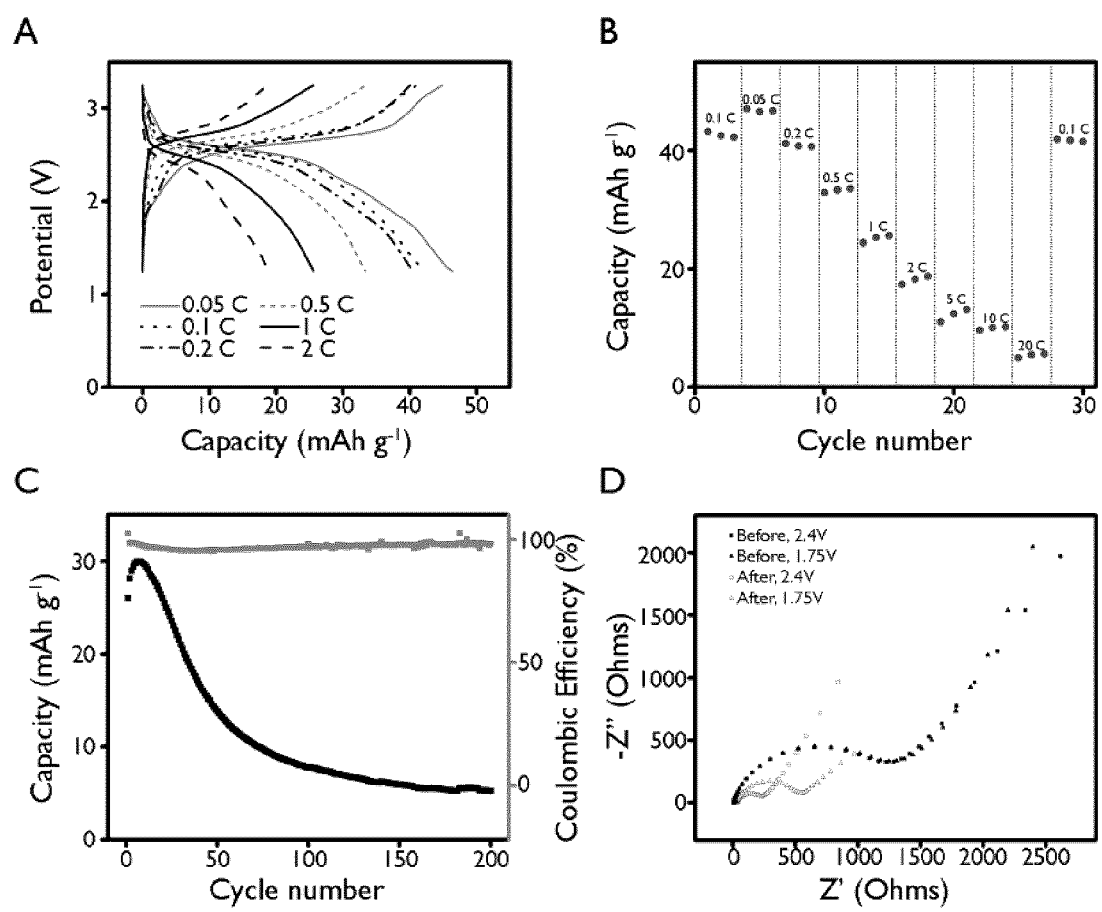
FIG. 10. Performance of battery with film cast with Formula 3 nanoparticles. (a) Galvanostatic charge/discharge curves at different C-rates, (b) rate capabilities of the battery, (c) cycling stability and coulombic efficiency, and (d) impedance spectroscopy at different states of charge before and after degradation.
Figure 11:
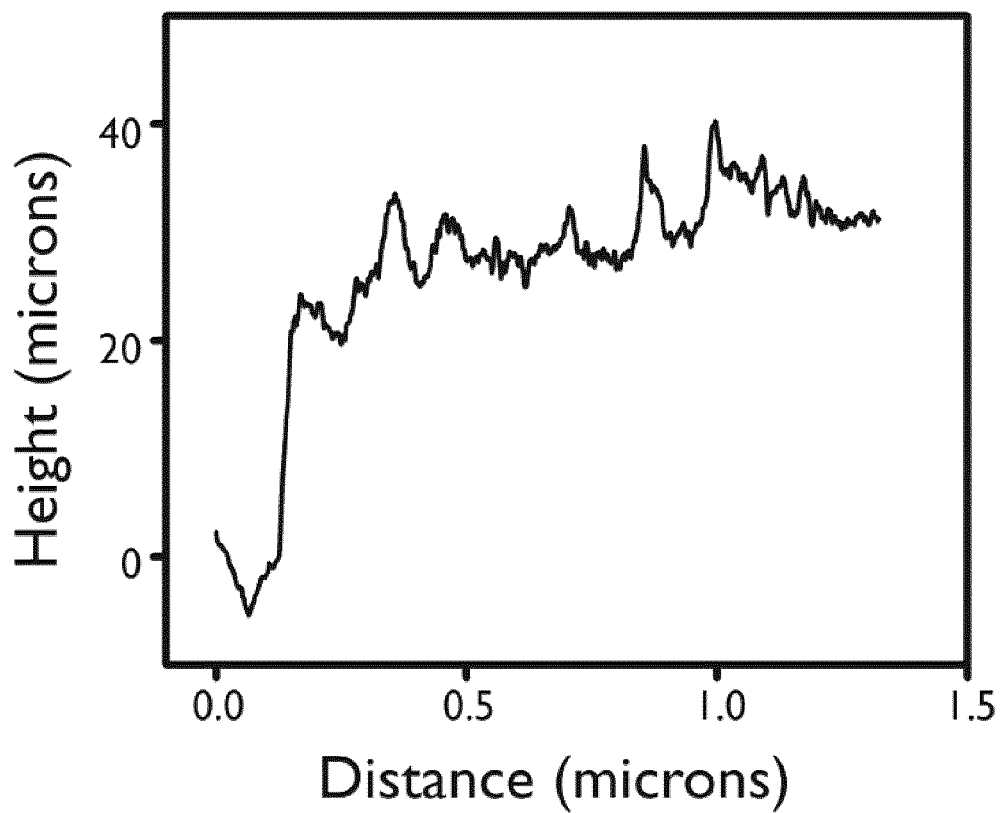
FIG. 11. Histogram of film height prepared by first mixing Formula 3 and CB in $CHCl_3$ and then mixing with PVdF in NMP.
Figure 12:
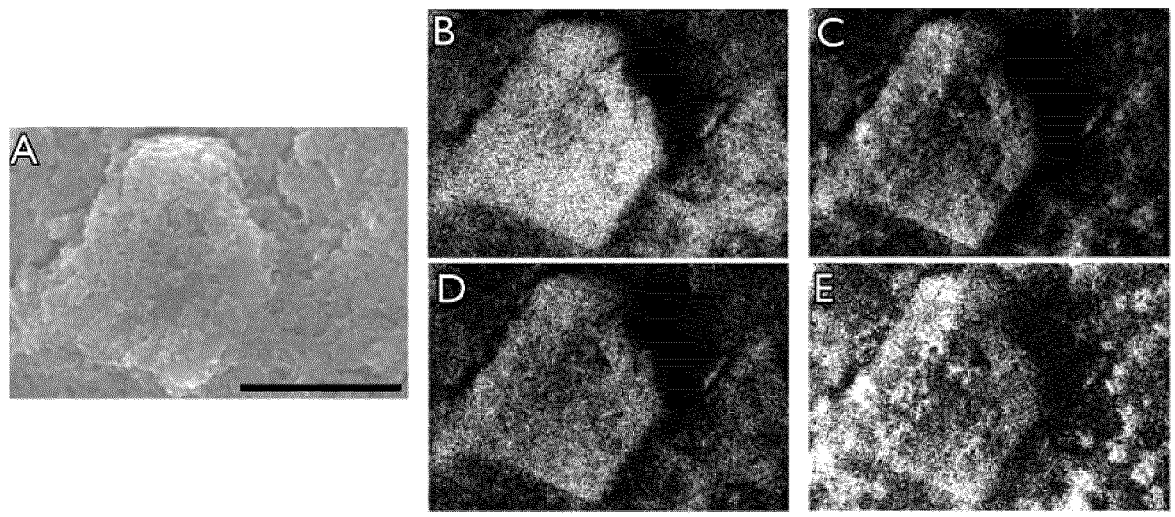
FIG. 12. EDX spectra of a film prepared by first mixing Formula 3 and CB in $CHCl_3$ and then mixing with PVdF in NMP. (a) SEM image, (b) C Kα image, (c) O Kα image, (d) N Kα image, and (e) F Kα image. Scale bar is 30 μm.

To study the flavin polymer as a lithium-ion battery cathode, we prepared a film consisting of Formula 3, carbon black (CB) and poly(vinylidene fluoride) (PVDF). Our first attempt was to prepare a methanolic suspension of polymer nanoparticles by flash precipitation. We found that this method gave large amounts Formula 3 aggregates in the composite (FIG. 2a,b) leading to low material usage as well as high charge transfer resistance of the electrode indicated by the impedance spectra (FIG. 10). The optimal mixing and performance was achieved by stirring a solution of CB and Formula 3 in chloroform, evaporating the solvent and then sonicating in a solution of PVDF and N-methyl-2-pyrrolidone (NMP). Casting using a 250 μm notch bar yielded films that are 30±4 μm thick determined by profilometry (FIG. 11). By first stirring the dissolved Formula 3 in chloroform with CB coats the carbon surface with Formula 3 allowing for a more homogenous film (FIG. 2c,d). The energy dispersive X-ray (EDX) spectra supports this, with a homogenous distribution of carbon, oxygen, nitrogen, and fluorine signals (FIG. 12). The Formula 3 coated CB structure was visualized in TEM images where the CB particles are covered by a thin layer of Formula 3 (FIGS. 2e,f).

Lithium-Ion Battery Characterization

FIG. 1 shows a scheme representing the battery architecture and incorporation of the electroactive redox polymer into the device. The battery includes a cell cathode casing 10, a spring spacer 11 that compresses the device, a spacer/current collector 12, a substrate 13 that the cathode material is cast on, the cathode 14 comprised of any of the molecules of Formulas 3 to 9 inclusive, the separator and electrolyte 15, the anode 16, the anode spacer/current collector 17, is a cell anode casing 18, and a gasket/O-ring 19 to hermetically seal the energy storage device.

Figure 3:
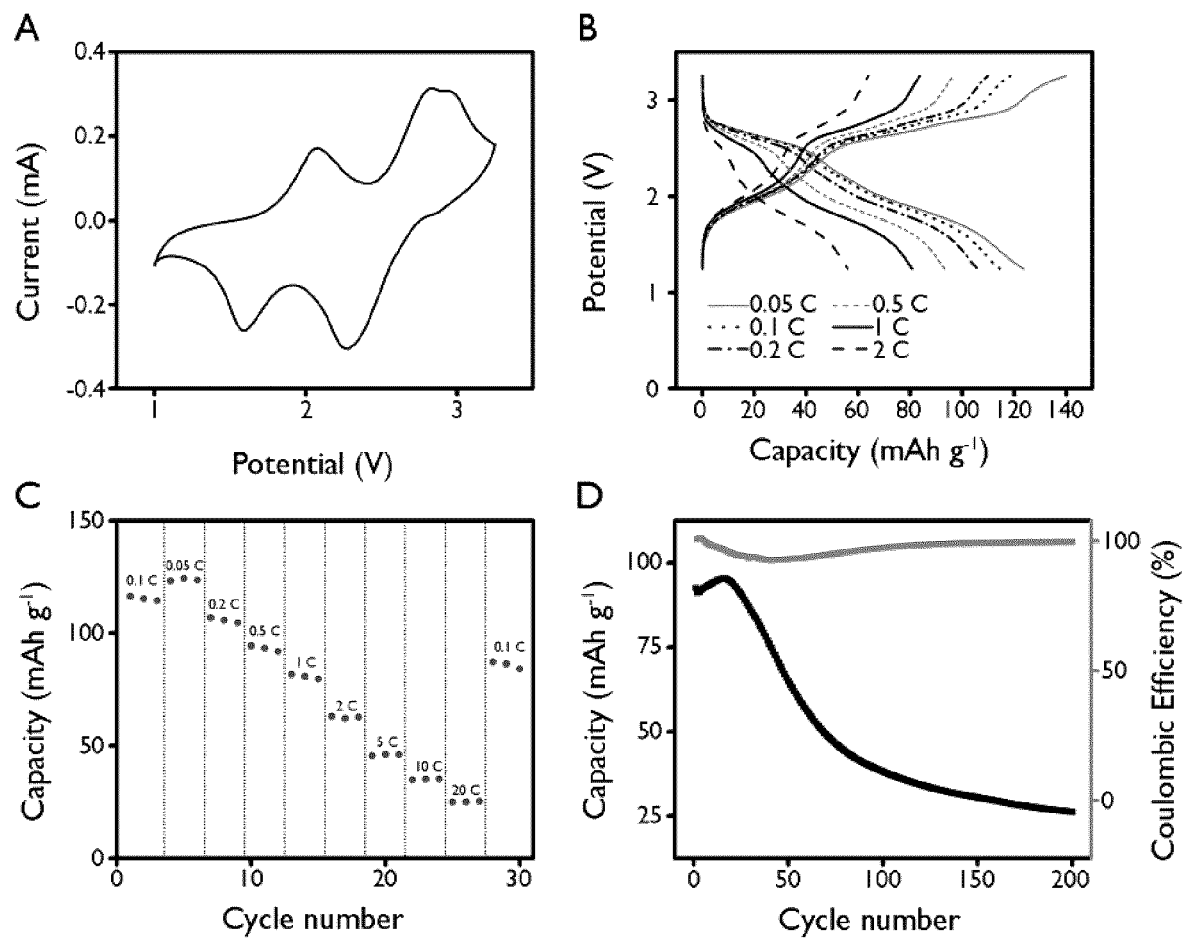
FIG. 3. Performance of Li-ion battery using Formula 3 as the cathode. (a) CV at 1 mV $s^{-1}$, (b) galvanostatic charge/discharge curves at different C-rates, (c) rate capabilities of the battery, and (d) cycling stability and coulombic efficiency. Performed using 1.0M $LiPF_6$ TEGDME using lithium as the anode.

We tested the electrochemical performance of the Formula 3 electrode by assembling a coin cell described in FIG. 1 with a lithium metal anode and a Celgard polypropylene lithium-ion separator, a commercially available CR2032 coin cell kit with a stainless steel cathode spacer and spring, stainless steel cathode and anode casing, and a rubber gasket, aluminum cathode current collector, and a copper anode current collector in a 1.0 M LiP $F_6$ tetraethylene glycol dimethyl ether (TEGDME) electrolyte (FIG. 3).

Two distinct redox peaks centered at 1.84 V and 2.55 V vs $Li/Li^+$ are observed (FIG. 3a). This is in contrast to the solution CV of Formula 3 using $TBAPF_6$ where only one redox peak is observed. The differences of the voltammograms are due to the counter-cation. The electrochemistry of flavins are highly dependent on the environment at which they are measured in, such as the pH, which can change the behavior of the flavin core from a one step, two electron reduction to a two-step, two electron reduction.

From the galvanostatic charge/discharge curves (FIG. 3b) we learn that the electrode has two sloping voltage plateaus at 2.65 V and 1.85 at a current of 0.1 C (0.1 C=14.4 mA $g^{-1}$, the amount of time to theoretically charge or discharge the cell in 10 hours), decreasing to 2.61 V and 1.76 V at 1 C (1 C=144 mA $g^{-1}$, the amount of time to theoretically charge or discharge the cell in 1 hours). The electrode has a 77 mAh $g^{-1}$ capacity at a current of 1 C corresponding to 53% of the theoretical capacity. Upon slowing down the current to 0.1 C, the capacity increases to 125 mAh $g^{-1}$ corresponding to 87% of the theoretical value (FIG. 3c). The high capacity at 0.1 C is due to the repeating unit being able to accept up to 4 electrons (2 per flavin motif).

Figure 13:
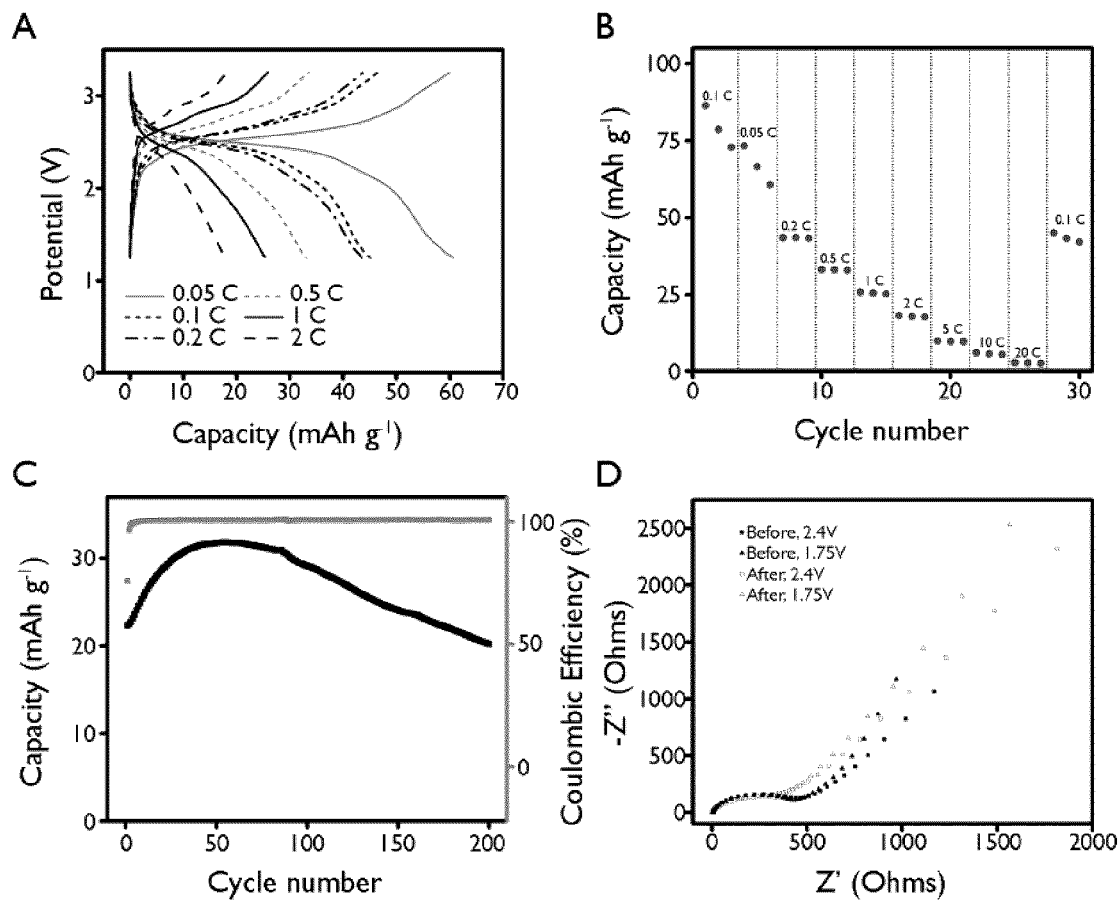
FIG. 13. Performance of battery cast by first mixing Formula 3 and CB in $CHCl_3$ then mixing with PVdF in NMP cycled in a 1.0M $LiPF_6$ EC:DMC 1:1 electrolyte. (a) Galvanostatic charge/discharge curves at different C-rates, (b) rate capabilities of the battery, (c) cycling stability and coulombic efficiency, and (d) impedance spectroscopy at different states of charge before and after degradation.

Upon cycling the battery the capacity decreases substantially (FIG. 3d). The most common mechanism of capacity fading in organic batteries is due to dissolution of the electrode where there are many examples. We have been able to rule out this mechanism of degradation by observing no color change in the TEGDME electrolyte after cycling. Additionally, when the cell is cycled in an electrolyte that is more soluble in, 1.0 M $LiPF_6$ ethylene carbonate:dimethyl carbonate (EC:DMC) 1:1, the stability is increased (FIG. 13). This suggests that there is another degradation mechanism that is contributing to the capacity fade. We can also rule out chemical degradation by examining the absorption spectra of Formula 3 before and after cycling (FIG. 4a).

Figure 4:
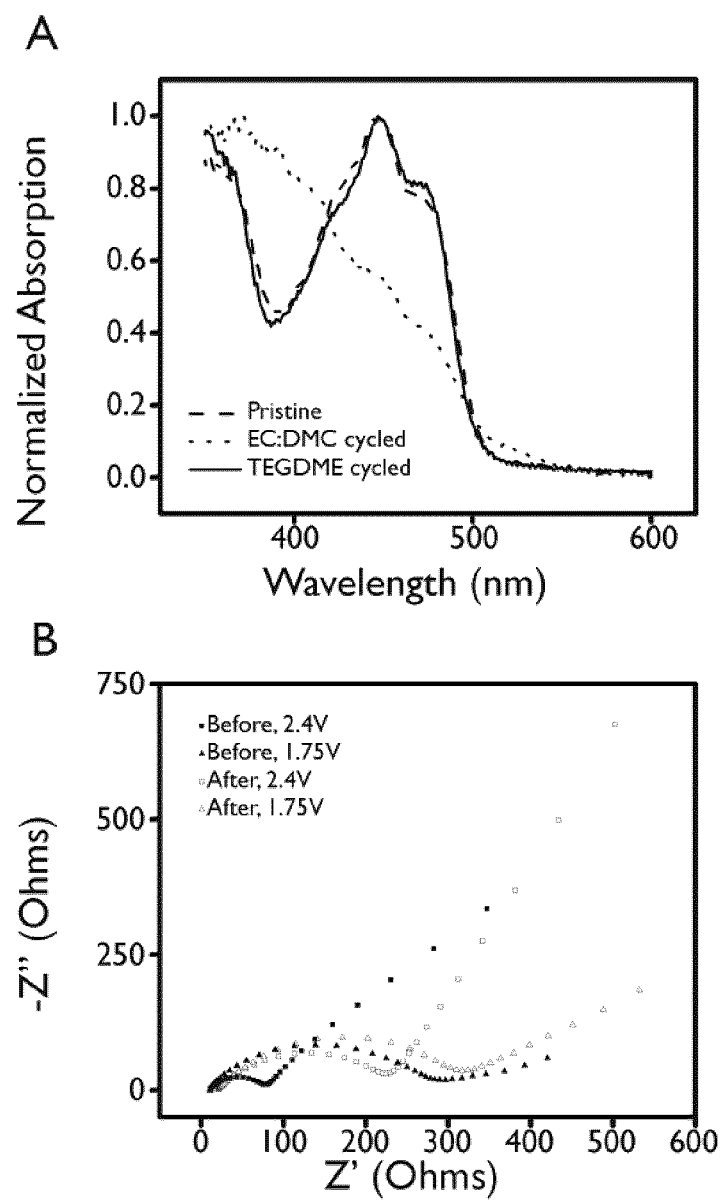
FIG. 4. (a) UV-Vis trace of disassembled cell cathodes extracted with $CHCl_3$. (b) Nyquist plots of cell cycled in 1.0M $LiPF_6$ TEGDME at different states of charge before and after degradation.

The optical absorption profiles are very similar for the sample extracted from a pristine electrode and one that has been cycled in the TEGDME electrolyte. For comparison, we tried to extract Formula 3 from the cell cycled in an EC:DMC electrolyte. Since Formula 3 is soluble in the EC:DMC electrolyte, there was very little of it to extract, resulting in the absence of the signature peaks in the spectra (FIG. 4). Although we cannot rule out small amounts of Formula 3 degradation in the TEGDME electrolyte upon cycling, this does not account for the large differences in capacity upon cycling. Another common mode of degradation for battery materials is delamination of the electrode from the current collector. This is unlikely because the electrode is fully intact after cycling and disassembly.

Figure 14:
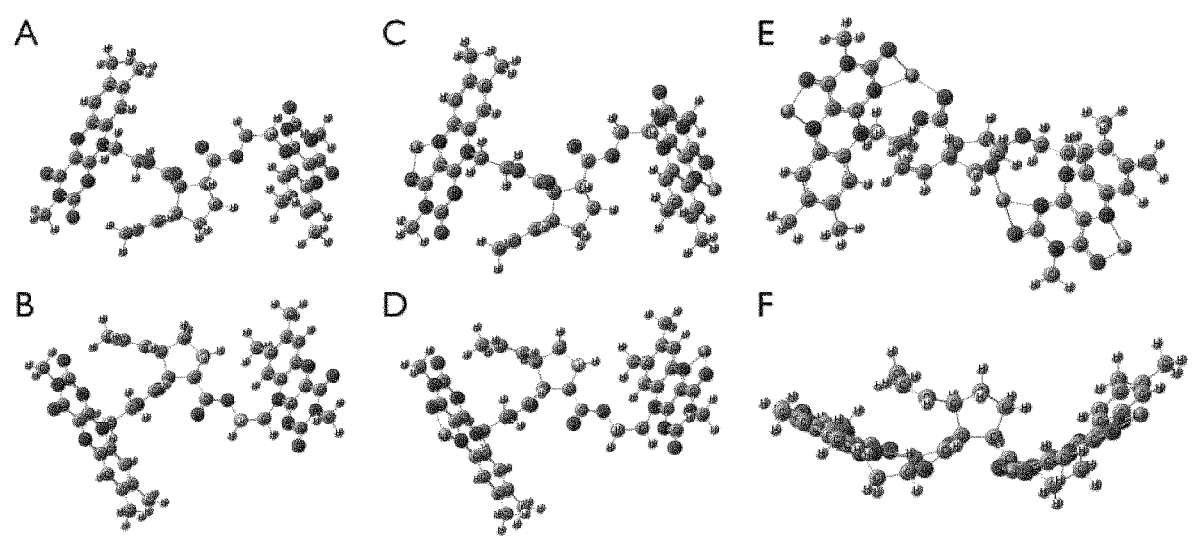
FIG. 14. Optimized geometries of a unimer of Formula 3 calculated by computational chemistry in the (a,b) neutral, (c,d) negative 2 state, and (e,f) negative 4 state. All charges in optimized geometries are balanced by Li ions.

We hypothesize that this capacity fading is likely due to local morphology changes that occur upon reduction, isolating the redox units in Formula 3 from the electrical conduction pathway provided by the CB particles. In order to test this, we performed geometry optimization calculations. The neutral and negative 2 compound of Formula 3 (1 electron balanced by 1 lithium ion on each flavin unit) have almost the same geometry (FIG. 14). However, upon reducing each flavin unit once more, the geometry changes significantly with the second lithium ion coordinating to flavin unit on Formula 3 as well as the carbonyl group of the ester linkage. We believe that this large change in structure isolates the redox units over time, manifesting itself into a significant capacity fade. This also changes the impedance of the electrode (FIG. 4b). The impedance spectra were measured at 2.40 V and 1.75 V in order to probe the resistances associated with charge transfer at each reduction before and after cycling. Before cycling, the charge transfer resistance, indicated by the diameter of the semicircle at high frequency, is greater at 1.75 V compared to 2.40 V indicating that there is a greater resistance for the second reduction, in line with the large structural change in order to accommodate the stabilization of the charged species. After cycling, the charge transfer resistances for both reductions increase significantly indicating that it is harder to reduce the species after the film has been cycled. This can be rationalized by the unfavourable morphology that the electrode takes on after cycling.

Figure 16:
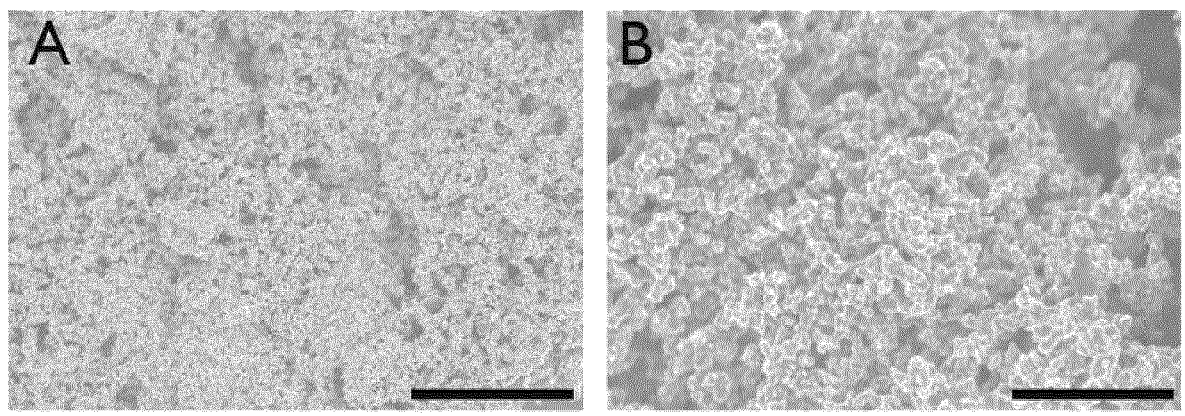
FIG. 16. SEM of electrodes after cycling. Scale bars are (a) 5 μm and (b) 1 μm.

SEM images taken of the cycled electrode do not exhibit any large changes compared to the pristine sample (FIG. 16). The only observable differences are the appearance of small spots on the CB particles. Attempts to analyze these via EDX were unsuccessful. Powder x-ray diffraction (PXRD) does not show any differences between the cycled and uncycled films. There is only one significant peak in the PXRD corresponding to the spacing between the graphitic planes in the CB particles, occurring at 25-26°.

Discussion

In summary, the application of a pendant polymer using a poly(norbornene) backbone and a flavin pendant group as the redox active unit for lithium ion batteries is demonstrated. By mixing Formula 3 and the carbon additive in a solvent in which Formula 3 is soluble in allows for a homogenous dispersion of the composite materials, facilitating excellent electron transfer between the active material and the conductive carbon network without the use of expensive nanostructures. Additionally, the ability of Formula 3 to accept up to 4 electrons per repeating unit manifests itself into a high capacity of 125 mAh g$^{-1}$ at 0.1 C, 87% of the theoretical capacity. The low resistance of the electrode allows the plateau of the potential to remain almost constant at different C-rates, as demonstrated using galvanostatic charging and discharging. The capacity fade upon cycling is likely due to local morphological changes in Formula 3 structure as suggested by the geometry optimization calculations. As Formula 3 undergoes the second reduction on each flavin unit, coordination of the lithium counterion to the ester carbonyl group induces local changes in the structure that work to isolate the redox units from the electron conduction pathway. The large structural changes are supported by the large resistance associated with the second reduction in the impedance spectra. By using computational chemistry, we have predicted the changes in geometry that are associated with charging and discharging. The ability to tune the connectivity and spacer length with the help of computational chemistry by geometry optimization calculations allows the design of compounds that can afford higher stability by minimizing the structural change upon charging and discharging. We have identified targets that according to our calculations will perform much better than the test example. Additionally, we can tune the voltage of the battery by examining the energy levels of the compounds, provided by the geometry optimization calculation, in order to further improve the performance by synthetic chemistry. This work is currently underway. Our work demonstrates that simple modifications of biological molecules can render them useful for cheap, non-toxic energy storage materials with high capacity. Additionally, we highlight the importance of structural change between the different oxidation states of the polymer due to coordination of the counter ion and its effect on the overall stability of organic lithium-ion electrodes.

Formulas 3 to 9 can also be useful as electroactive materials for electrochemical energy storage devices such as but not limited to a lithium-ion battery, a sodium-ion battery, a magnesium-ion battery, an aluminum-ion battery, a potassium-ion battery, a metal-sulfur battery, a metal-air battery, a solid-state battery, a flow battery, an aqueous battery, a capacitor, a supercapacitor, a hybrid device combining electrode materials of any of the above devices, and a thin film battery that includes any of the above mentioned devices with a total device thickness of less than 5 millimeter but preferably less than 1 millimeter.

Due to their similar operation and configuration where a potential difference between the two electrodes drives an electrical current from one electrode, through an external circuit, and into the other electrode with a concomitant balance of charge on each electrode by ions in the electrolyte, Formulas 3 to 9 can be used providing a suitable counter or anode or cathode is used that provides a high enough potential difference for these events to occur. Due to the nature in which organic materials undergo redox chemistry with the relatively unspecific manner in respect to counter-ion charge balancing, they are more versatile than their inorganic counterparts such as metal oxides or phosphates that require ions of specific size and/or charge in order to function as useful electrodes. This allows them to be useful in a number of battery configurations and chemistries.

The energy storage devices may be constructed to have one or both of flexible mechanical properties and a customizable form factor. Here, flexible mechanical properties refer to the entire energy storage device possessing mechanical flexibility with a bending radius of at least 5 mm and a twisting angle of at least 15° while still maintaining greater than 90% of the device performance in an unbent or twisted state. A customizable form factor here refers to the ability to manufacture the entire device into a variety of shapes, sizes, and architectures such as patterned batteries, printed batteries, and batteries with unconventional architectures while still maintaining greater than 90% of the device performance when manufactured in a conventional battery architecture, size, and shape such as a coin cell or a pouch-type cell.

In addition to the above-mentioned energy storage devices that the present compounds may be used for, By taking advantage of the electroactive properties of these materials, it will be understood that these compounds may also be used as catalysts for, including but not limited to, hydrogenation, sulfoxidation, hydrogen peroxide addition, and oxidation and reduction of organic/inorganic molecules.

These materials may also be used for electrocatalysis, one example being for use in fuel cells, and other examples including electrocatalytic oxidation of biologically relevant molecules including but not limited to nicotinamide adenine dinucleotide, oxygen, dopamine, and ascorbic acid.

These materials may also be used for water splitting, taking advantage of the electrocatalytic properties of the materials. This would occur through electrocatalytic oxidation of water in an appropriate electrolytic solution to produce molecular oxygen and/or hydrogen peroxide. This could also occur through the electrocatalytic reduction of water in an appropriate electrolytic solution to produce molecular hydrogen.

They may also be used as fluorescent labels where a specific binding to the material by a biologically or commercially relevant substance including but not limited to cells, proteins, tissue, and/or organic molecules leads to the substance being fluorescently labelled by the material. Upon examination of the substance, detection of the fluorescence afforded to the substance by the herein reported materials would lead to a quantitative and/or qualitative result indicating whether binding has occurred, the degree of binding, and whether binding substances are present in the sample.

The inventors contemplate that these materials may be useful as a therapeutic agents, for example a drug delivery vessel, a drug, and/or a prodrug.

The foregoing description of the preferred embodiments of the present disclosure have been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A compound having a molecular structure according to Formula 1:

FORMULA 1

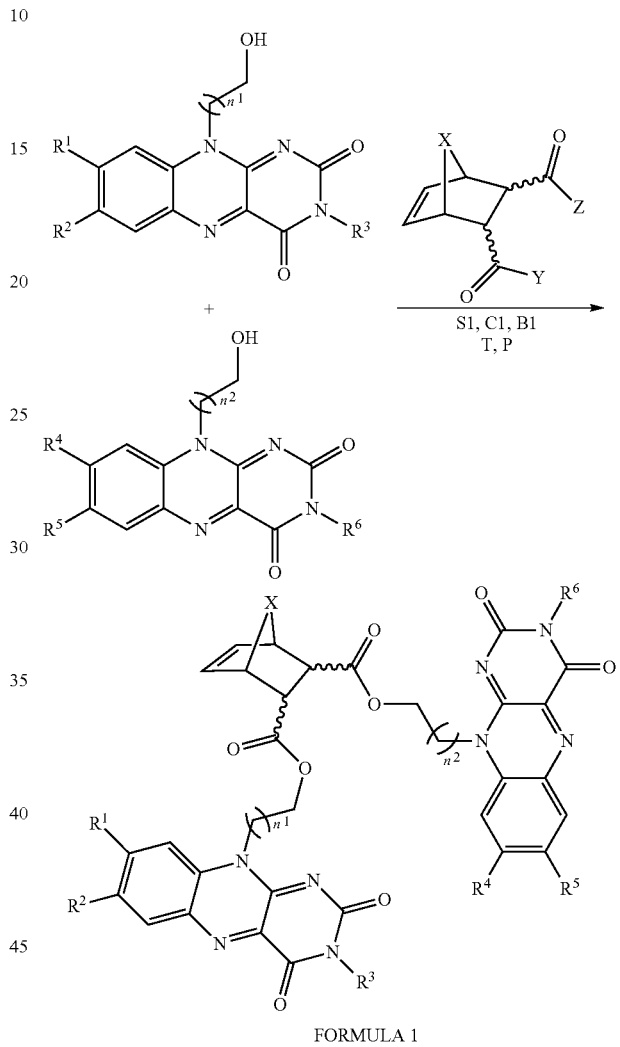

wherein $R^1$, $R^2$, $R^4$ and $R^5$ are independently a hydrogen atom, alkyl group, cyano group, nitro group, halogen, aromatic group or heteroaromatic group;

$R^3$ and $R^6$ are independently a hydrogen atom, alkyl group, aromatic group, heteroaromatic group or crosslinking agent, wherein the crosslinking agent is an ester, amide, alkyl, aryl, or any polymer thereof;

X is either a methylene or oxygen atom; and $n^1$ and $n^2$ are independently a number of repeat units ranging from 0 to 6.

2. The compound according to claim 1 wherein the alkyl group of $R^1$, $R^2$, $R^4$ and $R^5$ is independently a methyl, ethyl, propyl, isopropyl, or butyl, and the alkyl group of $R^3$ and $R^6$ is independently a methyl, ethyl, propyl, isopropyl, or butyl.

3. The compound according to claim 1 wherein $R^1$, $R^2$, $R^3$, $R^4$, $R^5$ and $R^6$ are methyl, X is a methylene, and $n^1$ and $n^2$ is equal to one (1).

4. A process for producing a compound according to claim 1 having a molecular structure according to FORMULA 1, comprising:

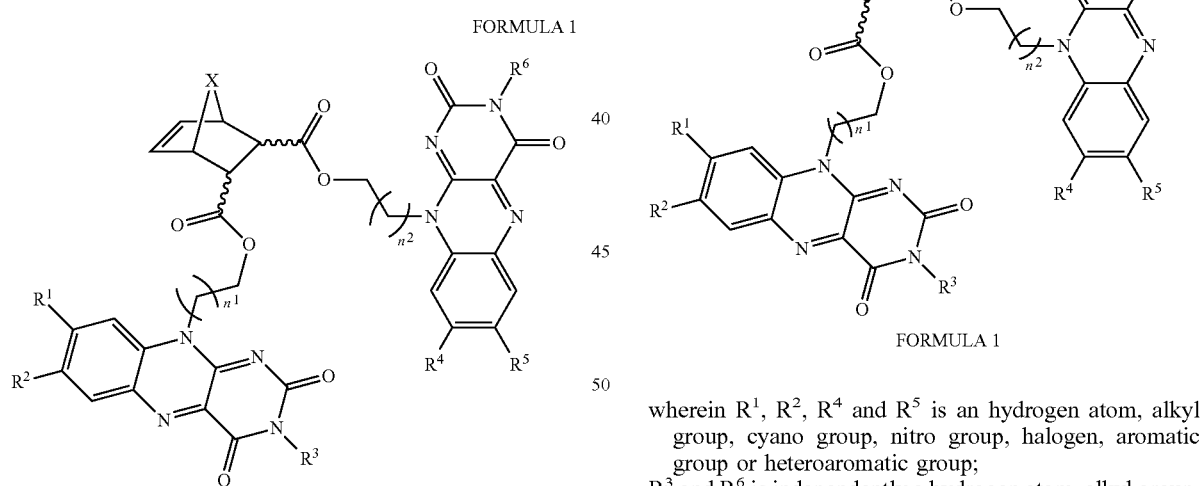

FORMULA 1 wherein $R^1$, $R^2$, $R^4$ and $R^5$ is an hydrogen atom, alkyl group, cyano group, nitro group, halogen, aromatic group or heteroaromatic group;

$R^3$ and $R^6$ is independently a hydrogen atom, alkyl group, aromatic group, heteroaromatic group or crosslinking agent, wherein the crosslinking agent is an ester, amide, alkyl, aryl, or any polymer thereof;

X is a methylene or oxygen atom;

$n^1$ and $n^2$ is independently a number of repeat units ranging from 0 to 6;

Z and Y is leaving groups that are eliminated in the reaction and replaced with the flavin groups;

S1 is a solvent;

C1 is a catalyst;

B1 is a base; and the temperature, T, is between −20 and 50 degrees Celsius and the pressure, P, is between 0.5 and 5 atmospheres.

5. The process according to claim 4 wherein Z and Y are any one of bromine, chlorine, iodine, tosyl, and/or carboxyl groups, S1 is selected within the group of CHCl3, dichloromethane, ether, ethyl acetate, dimethyl formamide, acetonitrile and any combination, C1 is DMAP and the base is any one of pyridine, triethylamine, aniline, indole, piperidine, pyrimidine, pyrrolidine, pyrrole, imidazole, 4-diazabicyclo[2.2.2]octane, and 1,8-diazobicyclo[5.4.0]undec-7-ene.

6. The process according to claim 4 wherein the alkyl group of $R^1$, $R^2$, $R^4$, and $R^5$ is independently a methyl, ethyl, propyl, isopropyl, or butyl, and the alkyl group of $R^3$ and $R^6$ is independently a methyl, ethyl, propyl, isopropyl, or butyl.

7. The process according to claim 4 wherein $R^1$, $R^2$, $R^3$, $R^4$, $R^5$, and $R^6$ is methyl, X is methylene, $n^1$ and $n^2$ equal one (1), S1 is $CH_2Cl_2$, C1 is DMAP, B1 is pyridine.

* * * * *